US012757974B2

(12) United States Patent
Kohatsu et al.

(10) Patent No.: US 12,757,974 B2
(45) Date of Patent: Oct. 13, 2026

(54) ARTICLE OF FOOTWEAR COMPRISING A SOLE MEMBER WITH APERTURE PATTERNS

(71) Applicant: NIKE, Inc., Beaverton, OR (US)

(72) Inventors: Shane S. Kohatsu, Portland, OR (US); Christopher S. Cook, Portland, OR (US); Bret Schoolmeester, Banks, OR (US)

(73) Assignee: NIKE, Inc., Beaverton, OR (US)

( * ) Notice: Subject to any disclaimer, the term of this patent is extended or adjusted under 35 U.S.C. 154(b) by 410 days.

(21) Appl. No.: 17/874,812

(22) Filed: Jul. 27, 2022

(65) Prior Publication Data

US 2022/0369766 A1 Nov. 24, 2022

Related U.S. Application Data

(60) Continuation of application No. 16/700,342, filed on Dec. 2, 2019, now Pat. No. 11,432,617, which is a division of application No. 14/722,782, filed on May 27, 2015, now Pat. No. 10,537,151.

(51) Int. Cl.

| | |
|---|---|
| ***A43B 13/18*** | (2006.01) |
| ***A43B 7/144*** | (2022.01) |
| ***A43B 7/1445*** | (2022.01) |
| ***A43B 7/1485*** | (2022.01) |
| ***A43B 13/14*** | (2006.01) |

(Continued)

(52) U.S. Cl.

CPC ............ *A43B 13/186* (2013.01); *A43B 7/144* (2013.01); *A43B 7/1445* (2013.01); *A43B 7/1485* (2013.01); *A43B 13/146* (2013.01); *A43B 13/181* (2013.01); *A43D 1/025* (2013.01); *A61B 5/1036* (2013.01)

(58) Field of Classification Search

CPC ................ A43B 13/186; A43B 13/146; A43B 13/181; A43B 13/206; A43B 7/1485; A43D 1/025; A61B 5/01036

USPC ...................................................... 36/3 B, 29

See application file for complete search history.

(56) References Cited

U.S. PATENT DOCUMENTS

| | | | |
|---|---|---|---|
| 1,785,410 | A | 12/1930 | Gilkerson |
| 2,150,057 | A | 3/1939 | Fisch |
| 2,885,797 | A | 5/1959 | Chrencik |

(Continued)

FOREIGN PATENT DOCUMENTS

| | | | | |
|---|---|---|---|---|
| CN | 203482948 U | | 3/2014 | |
| CN | 107822263 A | * | 3/2018 | ............. A43B 17/00 |

(Continued)

OTHER PUBLICATIONS

Sep. 20, 2016—(WO) ISR & WO—App. PCT/US16/031995.

*Primary Examiner* — Katharine G Kane

(74) *Attorney, Agent, or Firm* — Banner & Witcoff, Ltd.

(57) ABSTRACT

An article of footwear includes an upper and a sole structure with a sole member. The sole member can be manufactured using a customized cushioning sole system. A user's foot morphology and/or preferences may be used to design the sole member. The sole member can include a set of pinpoint apertures that are formed along the outer surface of the sole member to form at least a first distribution of apertures associated with a first density and a second distribution of apertures associated with a second density, wherein the first density is greater than the second density.

20 Claims, 15 Drawing Sheets

(51) Int. Cl.
*A43D 1/02* (2006.01)
*A61B 5/103* (2006.01)

(56) References Cited

U.S. PATENT DOCUMENTS

| | | | |
|---|---|---|---|
| 2,983,056 | A | 5/1961 | Murawski |
| 3,253,355 | A | 5/1966 | Menken |
| 3,418,731 | A | 12/1968 | Anciaux |
| 3,785,646 | A | 1/1974 | Ruskin |
| 4,000,566 | A | 1/1977 | Famolare, Jr. |
| 4,235,026 | A | 11/1980 | Plagenhoef |
| 4,494,322 | A | 1/1985 | Klagmann |
| 4,523,393 | A | 6/1985 | Inohara |
| 4,624,061 | A | 11/1986 | Wezel et al. |
| 4,956,927 | A | 9/1990 | Misevich et al. |
| 5,044,096 | A | 9/1991 | Polegato |
| 5,068,983 | A | 12/1991 | Marc |
| 5,134,791 | A | 8/1992 | Gregory |
| 5,463,824 | A | 11/1995 | Bama |
| 5,699,627 | A | 12/1997 | Castro |
| 5,799,413 | A | 9/1998 | Argyris |
| 6,675,502 | B1 | 1/2004 | Chen |
| 6,874,252 | B2 | 4/2005 | Nakano |
| 7,032,328 | B2 | 4/2006 | Wilson et al. |
| 7,216,092 | B1 | 5/2007 | Weber et al. |
| 7,434,338 | B2 | 10/2008 | Pfander |
| 7,464,490 | B2 | 12/2008 | Lebo |
| 7,475,497 | B2 | 1/2009 | Hoffer et al. |
| 7,607,241 | B2 | 10/2009 | McDonald et al. |
| 7,707,746 | B2 | 5/2010 | Dean |
| 7,941,938 | B2 | 5/2011 | Yu et al. |
| 8,479,414 | B2 | 7/2013 | Baker et al. |
| 8,584,379 | B2 | 11/2013 | Baucom et al. |
| 8,713,819 | B2 | 5/2014 | Auger et al. |
| 8,752,307 | B2 | 6/2014 | Cooper et al. |
| 2003/0217485 | A1 | 11/2003 | Oishi et al. |
| 2004/0016148 | A1 | 1/2004 | Chen |
| 2004/0024645 | A1 | 2/2004 | Potter et al. |
| 2004/0159015 | A1 | 8/2004 | Dennis et al. |
| 2004/0168354 | A1 | 9/2004 | Nguyen |
| 2005/0071242 | A1 | 3/2005 | Allen et al. |
| 2008/0292179 | A1 | 11/2008 | Busch |
| 2009/0019648 | A1 | 1/2009 | Jones et al. |
| 2010/0126041 | A1 | 5/2010 | Francis |
| 2010/0199524 | A1 * | 8/2010 | Grun ........................ G01L 1/122 36/43 |
| 2011/0061263 | A1 | 3/2011 | Everz-Vaz |
| 2011/0099850 | A1 | 5/2011 | Van Dyck |
| 2011/0162234 | A1 | 7/2011 | Dean |
| 2011/0272085 | A1 | 11/2011 | Hoffer et al. |
| 2012/0180336 | A1 | 7/2012 | Sullivan et al. |
| 2013/0160223 | A1 | 6/2013 | Bier et al. |
| 2013/0219746 | A1 | 8/2013 | Chiu |
| 2013/0258085 | A1 | 10/2013 | Leedy et al. |
| 2014/0182049 | A1 | 7/2014 | Prust et al. |
| 2014/0182170 | A1 | 7/2014 | Wawrousek et al. |
| 2014/0223777 | A1 | 8/2014 | Whiteman et al. |
| 2014/0290094 | A1 | 10/2014 | Miner |
| 2014/0366399 | A1 | 12/2014 | Wakeland et al. |

FOREIGN PATENT DOCUMENTS

| | | | |
|---|---|---|---|
| DE | 202008006494 | U1 | 7/2008 |
| EM | 2031994 | A1 | 3/2009 |
| EM | 2433515 | A2 | 3/2012 |
| GB | 1512745 | A | 6/1978 |
| KR | 20140104210 | A | 8/2014 |
| WO | 99053785 | A1 | 10/1999 |
| WO | 2016022298 | A1 | 2/2016 |

* cited by examiner

ARTICLE OF FOOTWEAR COMPRISING A SOLE MEMBER WITH APERTURE PATTERNS

RELATED APPLICATION DATA

This application is: (a) a continuation of U.S. patent application Ser. No. 16/700,342 titled "Methods for Customizing Cushioning Sole Systems for Articles of Footwear," filed Dec. 2, 2019, which application is (b) a divisional application based on U.S. patent application Ser. No. 14/722,782 titled "Article of Footwear Comprising a Sole Member with Aperture Patterns," filed May 27, 2015 (now U.S. Pat. No. 10,537,151 B2, granted Jan. 21, 2020). Each of U.S. patent application Ser. No. 14/722,782 and U.S. patent application Ser. No. 16/700,342 is entirely incorporated herein by reference.

BACKGROUND

The present embodiments relate generally to articles of footwear, and in particular to articles with cushioning provisions and methods of making such articles.

Articles of footwear generally include two primary elements: an upper and a sole structure. The upper is often formed from a plurality of material elements (e.g., textiles, polymer sheet layers, foam layers, leather, synthetic leather) that are stitched or adhesively bonded together to form a void on the interior of the footwear for comfortably and securely receiving a foot. More particularly, the upper forms a structure that extends over instep and toe areas of the foot, along medial and lateral sides of the foot, and around a heel area of the foot. The upper may also incorporate a lacing system to adjust fit of the footwear, as well as permitting entry and removal of the foot from the void within the upper. In addition, the upper may include a tongue that extends under the lacing system to enhance adjustability and comfort of the footwear, and the upper may incorporate a heel counter.

The sole structure is secured to a lower portion of the upper so as to be positioned between the foot and the ground. In athletic footwear, for example, the sole structure includes a midsole and an outsole. The various sole structure components may be formed from a polymer foam material that attenuates ground reaction forces (i.e., provides cushioning) during walking, running, and other ambulatory activities. The sole structure may also include fluid-filled chambers, plates, moderators, or other elements that further attenuate forces, enhance stability, or influence the motions of the foot, for example.

SUMMARY

In one aspect, the present disclosure is directed to a sole member for an article of footwear, comprising a sole member, the sole member including an outer surface, and the outer surface comprising an upper surface and a lower surface. The sole member has an interior portion, where the interior portion is disposed between the upper surface and the lower surface, as well as a forefoot region and a heel region. Furthermore, the sole member has a set of apertures, where at least one aperture of the set of apertures is a blind-hole aperture, and where each aperture of the set of apertures is disposed along a portion of the outer surface of the sole member. Each aperture of the set of apertures has a cross-sectional diameter, and at least a portion of the set of apertures are arranged along the outer surface of the sole member to comprise a first column of apertures. The first column of apertures extends from the forefoot region to the heel region, and the first column of apertures includes at least a first aperture, a second aperture disposed adjacent to the first aperture, and a third aperture disposed adjacent to the second aperture. In addition, the first aperture has a first cross-sectional diameter, the second aperture has a second cross-sectional diameter, and the third aperture has a third cross-sectional diameter, where the first cross-sectional diameter is smaller than the second cross-sectional diameter, and where the second cross-sectional diameter is smaller than the third cross-sectional diameter.

In another aspect, the present disclosure is directed to a sole member for an article of footwear, comprising a sole member, the sole member including an outer surface, and the outer surface comprising an upper surface and a lower surface. The sole member has a forefoot region and a heel region. Furthermore, the sole member has a set of apertures, where each aperture of the set of apertures is a blind-hole aperture, and where at least a portion of the set of apertures is disposed along a portion of the outer surface of the sole member to form a first column of apertures. The first column of apertures extends from the forefoot region to the heel region. In addition, each aperture of the set of apertures is associated with a cross-sectional diameter, where the size of a majority of the apertures comprising the first column of apertures generally increases in a direction approaching a midfoot region of the sole member.

In another aspect, the present disclosure is directed to a sole member for an article of footwear, comprising a sole member, the sole member including an outer surface, and the outer surface comprising an upper surface and a lower surface. The sole member also has a set of pinpoint apertures, where each aperture of the set of pinpoint apertures is a blind-hole aperture, and where the set of pinpoint apertures are disposed along the outer surface of the sole member to form at least a first distribution of apertures and a second distribution of apertures. Furthermore, the first distribution of apertures is associated with a first density, the second distribution of apertures is associated with a second density, and the first density is greater than the second density.

In another aspect, the present disclosure is directed to a method for customizing a cushioning sole system for an article of footwear, the method comprising obtaining information related to a pressure distribution of a wearer's foot, and producing a first pattern comprising a first set of apertures arranged to form at least a first column of apertures. The method further includes generating instructions to form the first pattern in a sole member, and executing the instructions to form the first set of apertures in the sole member, where each aperture of the first column of apertures increases in cross-sectional diameter in a direction approaching a center of the sole member.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

Figure 1:
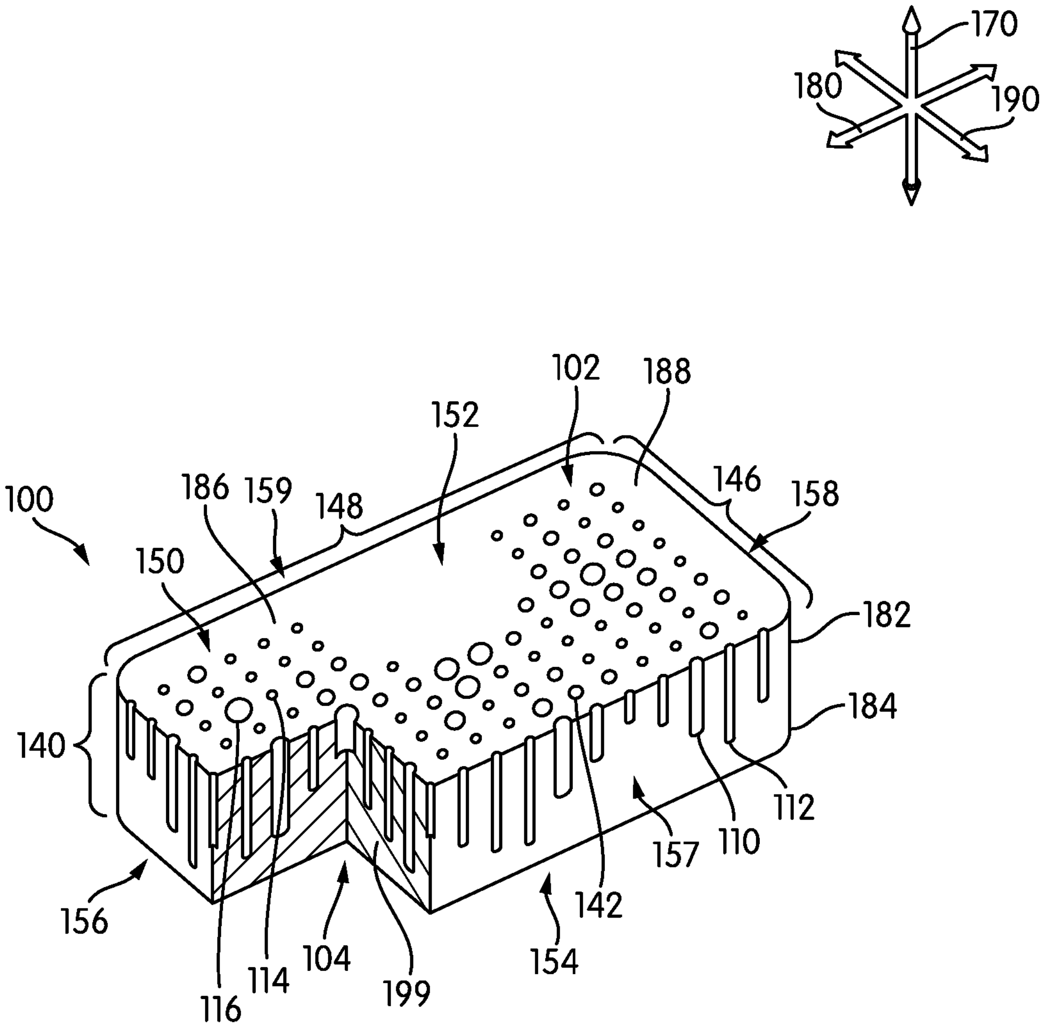
FIG. 1 is an isometric view of an embodiment of a cushioning element including apertures.

FIG. 1 depicts an embodiment of a portion of a cushioning element. A cushioning element can include provisions for increasing flexibility, fit, comfort, and/or stability during deformation or use of the cushioning element or article incorporating the cushioning element. Some of the embodiments of cushioning elements as disclosed herein may be utilized in various articles of apparel. In one embodiment, the cushioning elements may be used in an article of footwear. For example, as discussed in further detail below, in one embodiment, portions of a sole structure or sole member may incorporate or otherwise include a cushioning element.

For consistency and convenience, directional adjectives are also employed throughout this detailed description corresponding to the illustrated embodiments. The term "lateral" or "lateral direction" as used throughout this detailed description and in the claims refers to a direction extending along a width of a component or element. For example, a lateral direction may be oriented along a lateral axis 190 of a foot (see FIG. 5), which axis may extend between a medial side and a lateral side of the foot. Additionally, the term "longitudinal" or "longitudinal direction" as used throughout this detailed description and in the claims refers to a direction extending across a length of an element or component (such as a sole member). In some embodiments, a longitudinal direction may be oriented along longitudinal axis 180, which axis may extend from a forefoot region to a heel region of a foot (see FIG. 5). It will be understood that each of these directional adjectives may also be applied to individual components of an article of footwear, such as an upper and/or a sole member. In addition, a vertical axis 170 refers to the axis perpendicular to a horizontal surface defined by longitudinal axis 180 and lateral axis 190.

FIG. 1 depicts an embodiment of a first cushioning element ("first element") 100. As shown in FIG. 1, in some embodiments, a cushioning element can include one or more apertures 150. For purposes of this description, apertures 150 are openings, apertures, holes, tunnels, or spaces that are disposed within the cushioning element. Generally, apertures 150 are initially formed along an exterior or outer surface of the cushioning element, and can extend any distance, and along any orientation, through an interior portion 199 (e.g., the thickness, breadth, or width) of the cushioning element. It should be understood that the terms exterior or outer surface with reference to a sole member do not necessarily indicate whether the sole member is actually exposed to the outer elements. Instead, outer surface or exterior surface refers to the outermost, outward-facing layer of the sole member. Interior portion 199 can be disposed between an upper surface 152, a lower surface 154, and a sidewall in some embodiments. Throughout the specification, it should be understood that characteristics being described as associated with a single aperture or aperture set can also characterize any other aperture or aperture set that may be referred to in the various embodiments.

The embodiments described herein may also include or refer to techniques, concepts, features, elements, methods, and/or components from: (a) U.S. patent application Ser. No. 14/722,758, filed May 27, 2015, titled "Article of Footwear Comprising a Sole Member with Apertures," (b) U.S. patent application Ser. No. 14/722,826, filed May 27, 2015, titled "Article of Footwear Comprising a Sole Member with Geometric Patterns," and (c) U.S. patent application Ser. No. 14/722,740, filed May 27, 2015, titled "Article of Footwear Comprising a Sole Member with Regional Patterns," the entirety of each application being herein incorporated by reference.

In different embodiments, cushioning elements may comprise any three-dimensional shape or geometry, including regular or irregular shapes. For example, cushioning elements may be substantially flat or narrow, and/or relatively thick or wide. The geometry and dimensions of a cushioning element can be configured for the application or exercise in which it will be used. For illustrative purposes, in FIG. 1, first element 100 has a generally oblong rectangular three-dimensional shape. Furthermore, for purposes of reference, as shown in FIG. 1, each cushioning element may include an upper surface 152 and a lower surface 154 that is disposed opposite of upper surface 152. In some cases, upper surface 152 can be disposed adjacent to or joined to another component, such as an upper (see FIG. 12). In addition, in some cases, lower surface 154 or upper surface 152 can be a ground contacting surface. However, in other cases, lower surface 154 may be disposed adjacent to another material (such as an outsole). The cushioning elements can further include additional exterior-facing surfaces. For example, as shown in FIG. 1, first element has four sidewalls, including a first side 156, a second side 157, a third side 158, and a fourth side 159. First side 156, second side 157, third side

158, and fourth side 159 may extend between upper surface 152 and lower surface 154. In addition, cushioning elements include a thickness 140 extending between upper surface 152 and lower surface 154 along vertical axis 170, and a width 146 extending from second side 157 to fourth side 159 along lateral axis 190, as well as a length 148 extending along longitudinal axis 180 from first side 156 to third side 158. As noted in FIG. 1, thickness 140 may include an upper portion 182 and a lower portion 184. Width 146 may include a forward portion 192 and a rear portion 194. Furthermore, length 148 may include a first side portion 186 and a second side portion 188. Upper surface 152, lower surface 154, and sidewalls as depicted herein are associated with an outer surface of the cushioning elements.

It should be understood that other embodiments can have a fewer or greater number of exterior surfaces, and that the cushioning elements and the different regions of cushioning elements shown herein are for illustrative purposes only. In other embodiments, cushioning elements may include any contours, and may be any size, shape, thickness, or dimension, including regular and irregular shapes.

In some embodiments, apertures 150 have a rounded shape. In other embodiments, apertures 150 may include a wide variety of other geometries, including regular and irregular shapes. Apertures 150 may have a cross-sectional shape that is round, square, or triangular, for example. In some embodiments, apertures 150 may have a variety of geometric shapes that may be chosen to impart specific aesthetic or functional properties to a cushioning element.

In some cases, apertures 150 can be provided on or through lower surface 154 or upper surface 152 of the cushioning element. In other cases, apertures 150 can be provided on or through a side surface of the cushioning element. In one embodiment, apertures 150 can be provided on or through the side surfaces (for example, along first side 156, second side 157, third side 158, and/or fourth side 159) of the cushioning element as well as on lower surface 154 and upper surface 152 of the cushioning element.

In some embodiments, apertures 150 can provide means for decoupling or softening portions of a cushioning element in order to enhance its cushioning characteristics. For purposes of this disclosure, cushioning characteristics refer to the degree of fit, flexibility, cushioning, responsiveness, comfort, resilience, shock absorption, elasticity, and/or stability present in a portion of an element. For example, in some cases, apertures 150 can be formed in side portions and a lower portion of a cushioning element to reduce the cross sectional profile of the element at particular regions and/or to facilitate increased flexibility between various portions of the element. In one embodiment, apertures 150 can be applied to side portions and an upper portion to form regions between adjacent portions of the element that articulate or bend with respect to one another.

Thus, in the present embodiments, the operation of the cushioning elements can involve providing a material variance in the element. The material variance can be accomplished by providing voids (apertures) which can comprise cut-outs through the cushioning element. As will be described below with respect to FIG. 10, the cut-outs can involve a removal of material from the element, thereby providing softer and/or cushioned regions in the portions that include the apertures.

Generally, apertures 150 can comprise various openings or holes arranged in a variety of orientations and in a variety of locations on or through the cushioning element. For example, as shown in FIG. 1, in some embodiments, a first aperture set 102 may include apertures 150 that extend in a direction generally aligned with vertical axis 170 through thickness 140 of first element 100. In a cutaway section 104 of first element 100 of FIG. 1, it can be seen that the apertures of first aperture set 102 begin along upper surface 152 and extend toward lower surface 154. Thus, apertures 150 of first aperture set 102 include a series of openings 142 (i.e., gaps or openings) along an exterior surface of first element 100. In FIG. 1, upper surface 152 comprises the exterior surface in which openings 142 (shown here as partially formed in cutaway section 104) are formed. As will be discussed further below, apertures 150 may extend from an initial hole along an exterior surface to form apertures of varying sizes and lengths through thickness 140 of a cushioning element. Apertures 150 may be blind-hole apertures in some embodiments, where only one end of each of the apertures is open or exposed, while the opposite end of each of the aperture remains enclosed within the thickness of the element (i.e., only one end of each aperture may be exposed on an exterior surface of the element).

In different embodiments, the number of apertures 150 comprising each set of apertures can vary. For example, in one embodiment, first aperture set 102 can comprise between 1 and 100 apertures, or more than 100 apertures. In another embodiment, first aperture set 102 can comprise between 40 and 70 apertures. In still other embodiments, first aperture set 102 can include more than 100 apertures. In addition, in some embodiments, first aperture set 102 can include between 1 and 30 apertures. Similarly, in some embodiments, first aperture set 102 can include a wide range of numbers of apertures 150. Thus, depending on the cushioning characteristics desired, there can be more apertures or fewer apertures than illustrated in any set of apertures formed in a portion of a cushioning element.

As noted above, in some embodiments, apertures 150 may extend various distances through a cushioning element. For example, as shown in FIG. 1, some apertures 150 of first aperture set 102 may not extend below upper portion 182 of first element 100. However, other apertures 150 may extend further downward, below upper portion 182 and into lower portion 184. For example, an aperture may extend from upper surface 152, and be disposed at least partially within lower portion 184. It should be understood that the various portions can differ from that shown here and are for reference purposes only. Thus, apertures 150 can include any length from zero to nearly the entire length, width, or height of the cushioning element (including a diagonal length). In cases where the cushioning element varies in geometry from the generally oblong rectangular shape shown in FIG. 1, apertures can be formed such that they extend up to the maximum length, thicknesses, breadth, or width associated with the cushioning element. Thus, in some embodiments, the length of each aperture can vary with the size or dimensions of the cushioning element.

Generally, the shape of one or more apertures 150 in a cushioning element can vary. In some cases, one or more apertures 150 may have a linear configuration or shape. In other cases, one or more apertures 150 may have a nonlinear configuration or shape. In the embodiment of FIG. 1, apertures 150 are shown having a generally linear shape, for example.

In different embodiments, the dimensions of one or more apertures 150 relative to one another can vary. For example, referring to FIG. 1, in some embodiments, the lengths of each aperture in first aperture set 102 can vary. For example, in one embodiment, apertures 150 of first aperture set 102 may be longer than other apertures 150 of first aperture set 102. Thus, in FIG. 1, a first aperture 110 has a smaller length than adjacent second aperture 112. In other cases, however, the lengths of each aperture in first aperture set 102 can vary in another manner. First aperture 110 may have a length that is substantially similar to or greater than the length of second aperture 112, for example. Thus, each aperture can have a length that differs from the length of other apertures, and apertures 150 located in different portions of a cushioning element can vary in length relative to one another. The length of an aperture can also vary with reference to longitudinal axis 180 and/or lateral axis 190. Some examples of this variety will be described further below.

Additionally, the size of each aperture can vary. For purposes of this description, the size of an aperture can refer to the cross-sectional diameter or size of an aperture. In some cases, the volume associated with the interior of an aperture can be correlated with the average cross-sectional diameter of the aperture. Referring to FIG. 1, in some cases, each aperture in first aperture set 102 can have a substantially similar size (e.g., cross-sectional diameter). In other cases, two or more apertures in first aperture set 102 can have substantially different sizes. For example, a third aperture 114 has a size that is smaller than the size of adjoining fourth aperture 116. In other cases, however, the sizes of each aperture in first aperture set 102 can vary in another manner. Third aperture 114 may have a size that is substantially similar to or greater than the size of fourth aperture 116, for example. Thus, each aperture can have a size that differs from the size of other apertures, and apertures 150 located in different portions of a cushioning element can vary in size relative to one another. In other cases, the size of each aperture can vary with the size of the cushioning element. It should be understood that the size of an aperture can vary throughout a single aperture, such that one region of an aperture is larger or smaller than another region of the same aperture. However, in other embodiments, the size of an aperture may remain substantially constant throughout the length of the aperture. Some examples of this variety will be described further below.

In some embodiments, apertures on different portions of a cushioning element can be generally parallel with one another with respect to another surface or side of the element. In some cases, apertures extending from the same surface of a cushioning element may be generally parallel with one another, such that they do not intersect. In other words, the apertures may be generally oriented in a similar direction. For example, apertures formed on lower surface 154 or upper surface 152 may be similarly oriented in a direction generally aligned with vertical axis 170. Thus, in different embodiments, apertures 150 may be associated with approximately similar longitudinal, lateral, or vertical orientations. In other embodiments, however, apertures on the side surfaces may not be parallel with one another. In one example, there may be apertures with openings 142 on first side 156 that are oriented in one direction, and apertures with openings 142 on first side 156 that are oriented along a different direction. Furthermore, it will be understood that in some embodiments, only some apertures may be generally aligned through upper portion 182, lower portion 184, first side portion 186, second side portion 188, forward portion 192, and/or rear portion 194, while other apertures disposed throughout the cushioning element may not be aligned. Therefore it should be understood that while the embodiment of FIG. 1 shows apertures 150 having lengths extending along vertical axis 170, apertures can also be oriented so that they lie along any other direction (e.g., a horizontal, diagonal or non-planar direction). For example, in some embodiments, apertures can form an angle less than 90 and greater than 0 degrees with respect to vertical axis 170, lateral axis 190, and/or longitudinal axis 180. In some cases, apertures can form an angle between 30 and 60 degrees with respect to vertical axis 170, lateral axis 190, and/or longitudinal axis 180.

Figure 2:
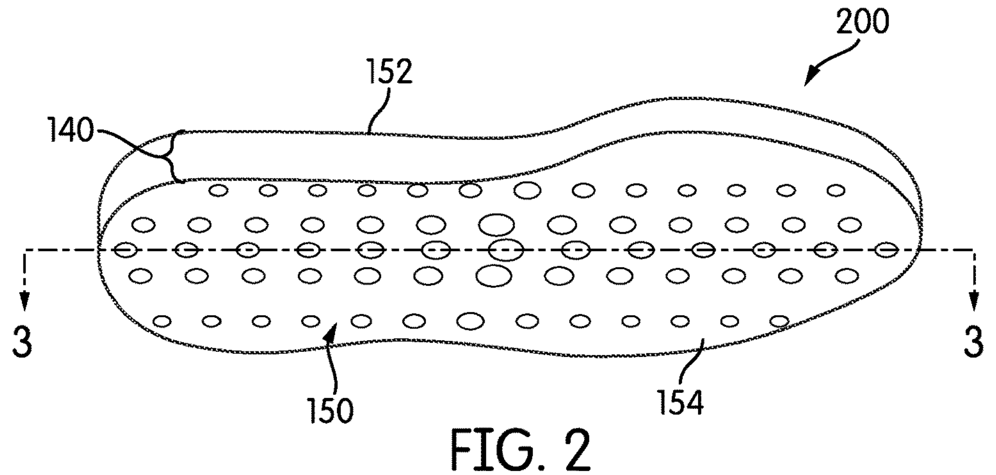
FIG. 2 is an isometric bottom view of an embodiment of a sole member comprising a cushioning element.
Figure 3:
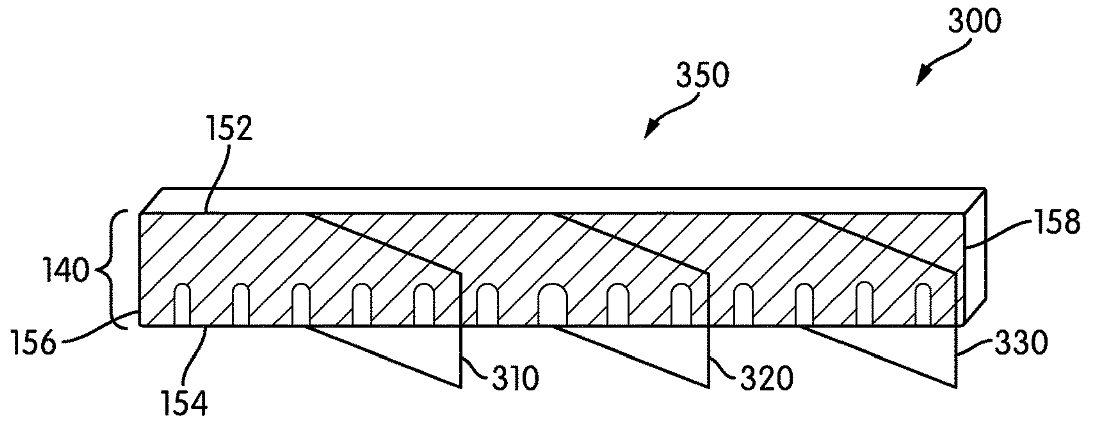
FIG. 3 is an isometric view of an embodiment of a cushioning element including apertures in an unloaded state.
Figure 4:
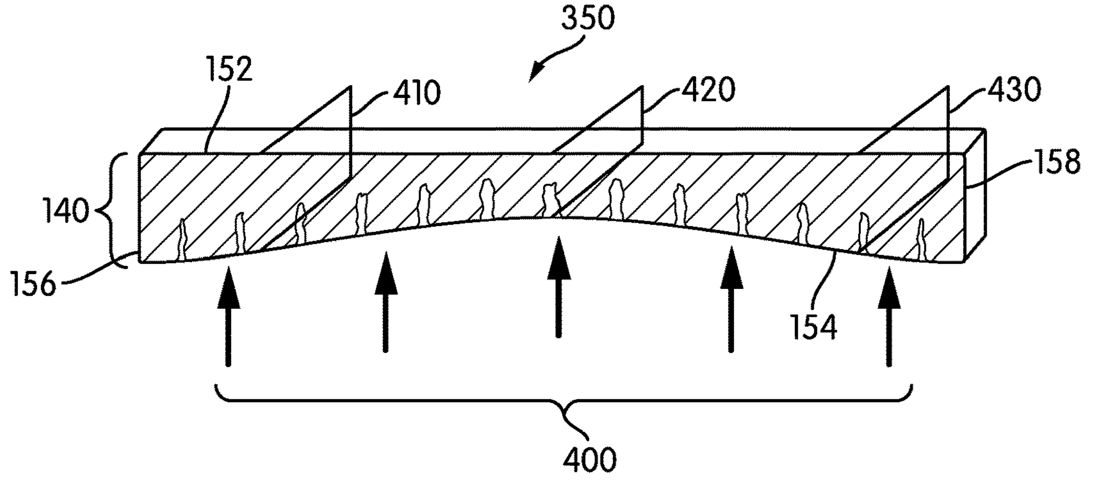
FIG. 4 is an isometric view of an embodiment of a cushioning element including apertures experiencing deformation.

As a result of the inclusion of different possible configurations of apertures 150, a cushioning element may have varying responsiveness to forces. In other words, apertures 150 can be disposed in a pattern that can help attenuate ground reaction forces and absorb energy, imparting different cushioning characteristics to the element. In the embodiments of FIGS. 2-4, a sequence of images representing possible responses of the cushioning elements under a load are shown.

For purposes of providing a contextual example to the reader, FIG. 2 depicts an embodiment of a first sole member 200. In FIG. 3, a cross section taken along the line 3-3 of FIG. 2 in first sole member 200 depicts an unloaded second cushioning element ("second element") 300. Second element 300 has a series of apertures 150 disposed along lower surface 154 and extending through thickness 140 at varying lengths. In some embodiments, apertures 150 may form a geometric pattern. In other words, apertures 150 may be arranged such that there is a predictable rise and fall to the sizes of the apertures throughout the cushioning element. Thus, in some embodiments, apertures 150 may be "tuned" to provide a smooth feel to the cushioning element, and improve comfort for a user. In FIG. 3, apertures 150 disposed nearer to third side 158 are smaller than apertures 150 disposed nearer toward a center 350 of second element 300. Furthermore, apertures 150 disposed nearer to first side 156 are also smaller than apertures 150 disposed nearer toward center 350. In FIGS. 3-4, apertures 150 increase in size as they approach center 350 of second element 300, and then generally decrease in size as they move further away from center 350. A regular arrangement as shown in second element 300 may provide more consistent cushioning for a user in some cases. However, it should be understood that, in other embodiments, apertures 150 may have a random height and/or size arrangement.

For purposes of convenience, heights are associated with different portions of second element 300. In FIG. 3, a first height 310, a second height 320, and a third height 330 are identified. First height 310 is associated with the portion of second element 300 toward first side 156, second height 320 is associated with the portion of second element 300 toward center 350, and third height 330 is associated with the portion of second element 300 toward third side 158. In FIG. 3, first height 310, second height 320, and third height 330 are substantially similar, such that thickness 140 is generally uniform through second element 300.

However, when second element 300 undergoes a first load 400 (represented by arrows), as shown in FIG. 4, the arrangement of apertures 150 can alter the responsiveness of the material. In FIG. 4, first load 400 is directed upward in a direction generally aligned with vertical axis 170 and distributed in a substantially constant, uniform manner over lower surface 154 of second element 300. As second element 300 experiences the force of first load 400, second element 300 can deform.

In some embodiments, when cushioning elements are compressed, they can deform in different ways. The deformation that occurs can be related to the location of any apertures, and/or the size and orientation of the apertures. Thus, apertures 150 may function together within the material of the cushioning element to provide variations in the relative stiffness, degree of ground reaction force attenuation, and energy absorption properties of the cushioning element. These cushioning characteristics may be altered to meet the specific demands of the activity for which the cushioning element is intended to be used, through the methods described herein.

When the compressive force of first load 400 is applied to second element 300, for example, the areas that include more apertures and/or apertures of greater size or length may deform to a greater extent than the portions of second element 300 that have fewer apertures and/or apertures of smaller size or length. As a result of the application of first load 400, the aperture openings may be compressed and deformed. In the region disposed proximate of center 350, where the sizes of the apertures are larger relative to other apertures, the degree of deformation is greater. In the regions nearest third side 158 and first side 156, where there are smaller sized apertures (relative to center 350 of second element 300), the deformation is not as great.

In some embodiments, the deformation that occurs throughout second element 300 can be measurable in part by the changed shape and height of second element 300 and/or the changed shape and heights of apertures 150. In FIG. 4, a fourth height 410, a fifth height 420, and a sixth height 430 can be identified. Fourth height 410 is associated with the portion of second element 300 toward first side 156, fifth height 420 is associated with the portion of second element 300 toward center 350, and sixth height 430 is associated with the portion of second element 300 toward third side 158. Thus, referring to FIGS. 3 and 4, in response to first load 400, the overall height of second element 300 is less. Specifically, fourth height 410 is less than first height 310, fifth height 420 is less than second height 320, and sixth height 430 is less than third height 330. Furthermore, the heights across second element 300 can differ, such that thickness 140 is generally non-uniform through second element 300. In other words, various contours can be formed along upper surface 152 where first load 400 has been applied.

The contours may vary in a manner generally corresponding to the arrangement of apertures 150 disposed in second element 300 in some embodiments. Thus, if apertures 150 are arranged in a repeating pattern, as seen with the apertures associated with first side 156 and the apertures associated with third side 158, which are arranged in a "mirrored" configuration, the deformation that occurs can be similarly mirrored, and the change in height may also reflect this mirroring. Thus, while fifth height 420 is less than either fourth height 410 or sixth height 430, fourth height 410 and sixth height 430 may be substantially similar. In other words, while some areas can be provided with different cushioning properties relative to other areas, there may also be areas that are provided with similar cushioning properties.

In some embodiments, the shape or orientation of the apertures may also change as a result of an applied force. Depending on the magnitude and the direction of the force(s) applied, the changes in area or shape may vary. For example, referring to FIG. 4, in one embodiment, second element 300 may be exposed to a force or load whereby apertures become deformed not only by becoming more compact, but also by curling or otherwise becoming increasingly non-linear and/or irregular. In one embodiment, the area or volume of an aperture may decrease when a compressive force is applied.

Thus, exposure to various forces may also produce a change in the shape or geometry, size, and/or height of cushioning elements and the apertures that may be disposed within the cushioning element. It should be understood that while first load 400 is shown as being generally uniform, other loads may be non-uniform. Depending on the magnitude and the direction of the force(s) applied, changes in area, volume, dimensions, and/or shape of the cushioning element may vary. In some embodiments, a different force may permit the cushioning element to expand in a lateral or longitudinal direction, such that the overall length of the element increases. In other embodiments, different forces may alter the responses of the cushioning element.

It should be noted that the various degrees of deformation described and shown here are for purposes of illustration. In some situations the cushioning element may not undergo compression to the extent depicted, or may deform more or less, depending on various factors such as the materials used in the production of the cushioning element, as well as its incorporation in other objects or articles. For example, if a cushioning element is joined or attached to a less reactive material, the compressive and/or expansive properties described herein may differ, or be limited. In some embodiments, when the cushioning element is joined to a strobel or other structure, the capacity of expansion may decrease. In some embodiments, the perimeter of the cushioning element may be fixed, e.g., bonded to a strobel layer or another sole layer. However, in such embodiments, the cushioning characteristics of the cushioning element may still facilitate increased flexibility and cushioning.

Furthermore, it should be understood that while second element 300 may experience various forces and deformation, the deformation may be elastic. In other words, once the load is removed or decreased, the cushioning element may recover and return to its original dimensions and/or shape, or to dimensions and/or a shape substantially similar to the original, unloaded configuration.

As noted above, the cushioning elements described herein may be utilized with various components or articles. For example, the degree of elasticity, cushioning, and flexibility of a sole component such as a sole member can be important factors associated with comfort and injury prevention for an article of footwear. FIGS. 5-8 depict an embodiment of a method of designing a customized sole member for an article of footwear.

Figure 5:
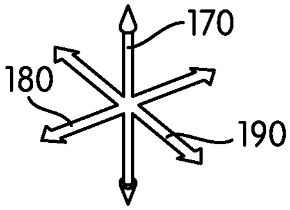
FIG. 5 illustrates an embodiment of the use of a device for obtaining three dimensional foot data.
Figure 5:
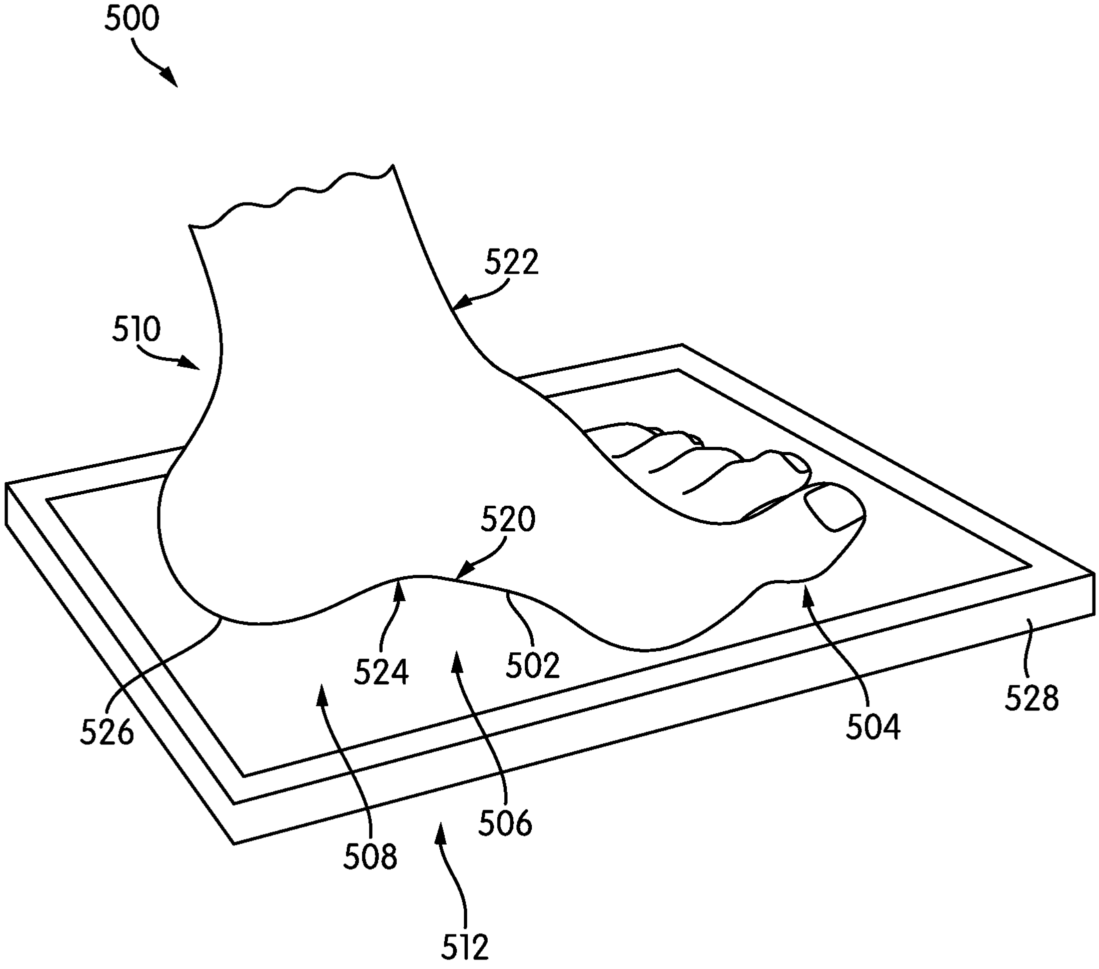

FIG. 5 shows the three-dimensional shape of a plantar surface 502 of a foot 500 being measured using a data collection apparatus 528. In some cases, data collection apparatus 528 can be a force platform. In other cases, data collection apparatus 528 can comprise one of the commercially available systems for measuring plantar pressure (e.g., Emed sensor platform, Pedar insole system, F-Scan system, Musgrave footprint system, etc.). Plantar pressure measurement systems can provide a means of obtaining specialized information regarding a foot that can be used to customize footwear for individuals. In some embodiments, the magnitude of pressure can be determined by dividing the measured force by the known area of the sensor or sensors evoked while the foot was in contact with the supporting surface in some embodiments.

For purposes of reference, foot 500, representations of foot 500, components associated with foot 500 (such as an article of footwear, an upper, a sole member, a computer aided design of foot 500, and other components/representations) may be divided into different regions. Foot 500 may include a forefoot region 504, a midfoot region 506 and a heel region 508. Forefoot region 504 may be generally associated with the toes and joints connecting the metatarsals with the phalanges. Midfoot region 506 may be generally associated with the metatarsals of a foot. Heel region

508 may be generally associated with the heel of a foot, including the calcaneus bone. In addition, foot 500 may include a lateral side 510 and a medial side 512. In particular, lateral side 510 and medial side 512 may be associated with opposing sides of foot 500. Furthermore, both lateral side 510 and medial side 512 may extend through forefoot region 504, midfoot region 506, and heel region 508. It will be understood that forefoot region 504, midfoot region 506, and heel region 508 are only intended for purposes of description and are not intended to demarcate precise regions of foot 500. Likewise, lateral side 510 and medial side 512 are intended to represent generally two sides of foot 500, rather than precisely demarcating foot 500 into two halves.

Figure 6:
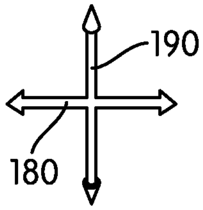
FIG. 6 schematically illustrates an embodiment of a virtual image of digitized three-dimensional foot data.
Figure 6:
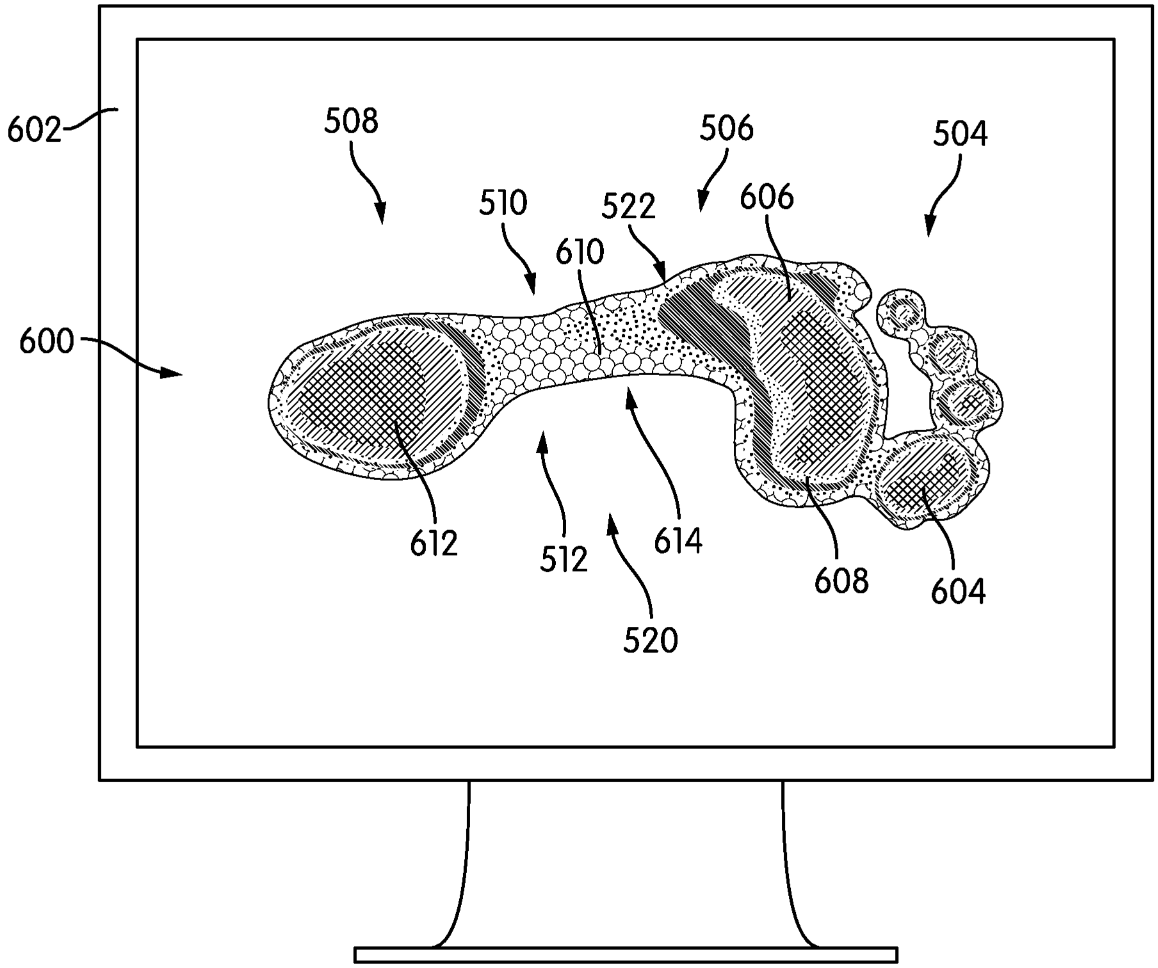

Furthermore, in the examples depicted in FIGS. 5 and 6, foot 500 and/or a virtual scan 600 of a foot may include a medial arch area 520, associated with an upward curve along medial side 512 of midfoot region 506, and a lateral arch area 522, associated with an upward curve along lateral side 510 of midfoot region 506. The region corresponding to lateral arch area 522 is best seen in FIG. 6, which illustrates a computer screen or virtual image of digitized three-dimensional foot data. As described below, the curvature of medial arch area 520 and lateral arch area 522 may vary from one foot to another. In addition, foot 500 includes a transverse arch 524 that extends along lateral axis 190 near forefoot region 504 along plantar surface 502. Foot 500 also includes a heel prominence 526, which is the prominence located in heel region 508 of foot 500. As shown in FIG. 5, foot 500 is illustrated as a left foot; however, it should be understood that the following description may equally apply to a mirror image of a foot or, in other words, a right foot.

Although the embodiments throughout this detailed description depict components configured for use in athletic articles of footwear, in other embodiments the components may be configured to be used for various other kinds of footwear including, but not limited to: hiking boots, soccer shoes, football shoes, sneakers, running shoes, cross-training shoes, rugby shoes, basketball shoes, baseball shoes as well as other kinds of shoes. Moreover, in some embodiments, components may be configured for various kinds of non-sports related footwear, including, but not limited to: slippers, sandals, high heeled footwear, loafers as well as any other kinds of footwear.

Components associated with an article of footwear are generally made to fit various sizes of feet. In the embodiments shown, the various articles are configured with approximately the same footwear size. In different embodiments, the components could be configured with any footwear sizes, including any conventional sizes for footwear known in the art. In some embodiments, an article of footwear may be designed to fit the feet of a child. In other embodiments, an article of footwear may be designed to fit the feet of an adult. Still, in other embodiments, an article of footwear may be designed to fit the feet of a man or a woman.

Referring to FIGS. 5 and 6, a first step of the present method is to collect data related to foot 500, such as using a barefoot pressure measurement or other data, from the foot being measured on data collection apparatus 528. Data collection apparatus 528 may include provisions for capturing information about an individual's feet. Specifically, in some embodiments, data collection apparatus 528 may include provisions to capture geometric information about one or more feet. This geometric information can include size (e.g., length, width and/or height) as well as three-dimensional information corresponding to the customer's feet (e.g., forefoot geometry, midfoot geometry, heel geometry and ankle geometry). In at least one embodiment, the captured geometric information for a customer's foot can be used to generate a three-dimensional model of the foot for use in later stages of manufacturing. In particular, the customized foot information can include at least the width and length of the foot. In some cases, the customized foot information may include information about the three-dimensional foot geometry. Customized foot information can be used to create a three-dimensional model of the foot. Embodiments may include any other provisions for capturing customized foot information. The present embodiments could make use of any of the methods and systems for forming an upper disclosed in Bruce, U.S. patent application Ser. No. 14/565,582, filed Dec. 10, 2014, titled "Portable Manufacturing System for Articles of Footwear," the entirety of which is herein incorporated by reference.

Some embodiments could use any of the systems, devices, and methods for imaging a foot as disclosed in Leedy et al., U.S. Patent Publication Number 2013/0258085, published Oct. 3, 2013, and titled "Foot Imaging and Measurement Apparatus," (previously U.S. patent application Ser. No. 13/433,463, filed Mar. 29, 2012), the entirety of which is herein incorporated by reference.

In FIG. 6, a screen 602 displays virtual scan 600 of plantar pressure distributions for foot 500. Scan 600 may provide a measured foot image or representation, including various distinct regions to indicate the pressures applied or experienced by foot 500 over its plantar surface 502. In one example, pressures can include a first pressure area 604, a second pressure area 606, a third pressure area 608, a fourth pressure area 610, and a fifth pressure area 612. An additional pressure area 614 is indicated where plantar surface 502 did not make an impressionable contact with the surface of data collection apparatus 528. In some embodiments, colors (not shown in FIG. 6) can be included in scan 600 to more readily distinguish variations within the measured pressure data. It should be noted that in other embodiments, different, fewer, or more pressure areas may be measured or indicated.

As seen in FIG. 6, in some embodiments, the data collected may include scan 600 of foot 500. In some embodiments, scan 600 may be used to assess the three-dimensional shape and obtain digital data in a two-dimensional or a three-dimensional reference frame. In other embodiments, scan 600 can provide a baseline shape for a footwear component. In one embodiment, three-dimensional scanned images may be used to measure the overall shape of a person's feet, and obtain two-dimensional measurements such as an outline, length, and width of foot 500. Obtaining foot geometry can establish a baseline record for the person in one embodiment. In some embodiments, other input may also be provided to supplement information regarding the person being measured. In different embodiments, additional data such as toe height information may also be obtained. In other embodiments, plaster casts of a person's foot may be taken and digitized. Additionally, other digital or imaging techniques which may be employed to capture two and three-dimensional foot shape and profile can be used to construct and/or supplement scan 600. In other embodiments, the person whose foot is being measured may provide answers to questions describing the person's physical characteristics, limitations, preferences, and/or personal lifestyle, which may impact design of the various parts described herein.

Figure 7:
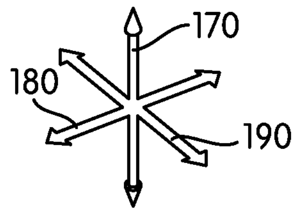
FIG. 7 schematically illustrates an embodiment of a virtual image of a template for a sole member.
Figure 7:
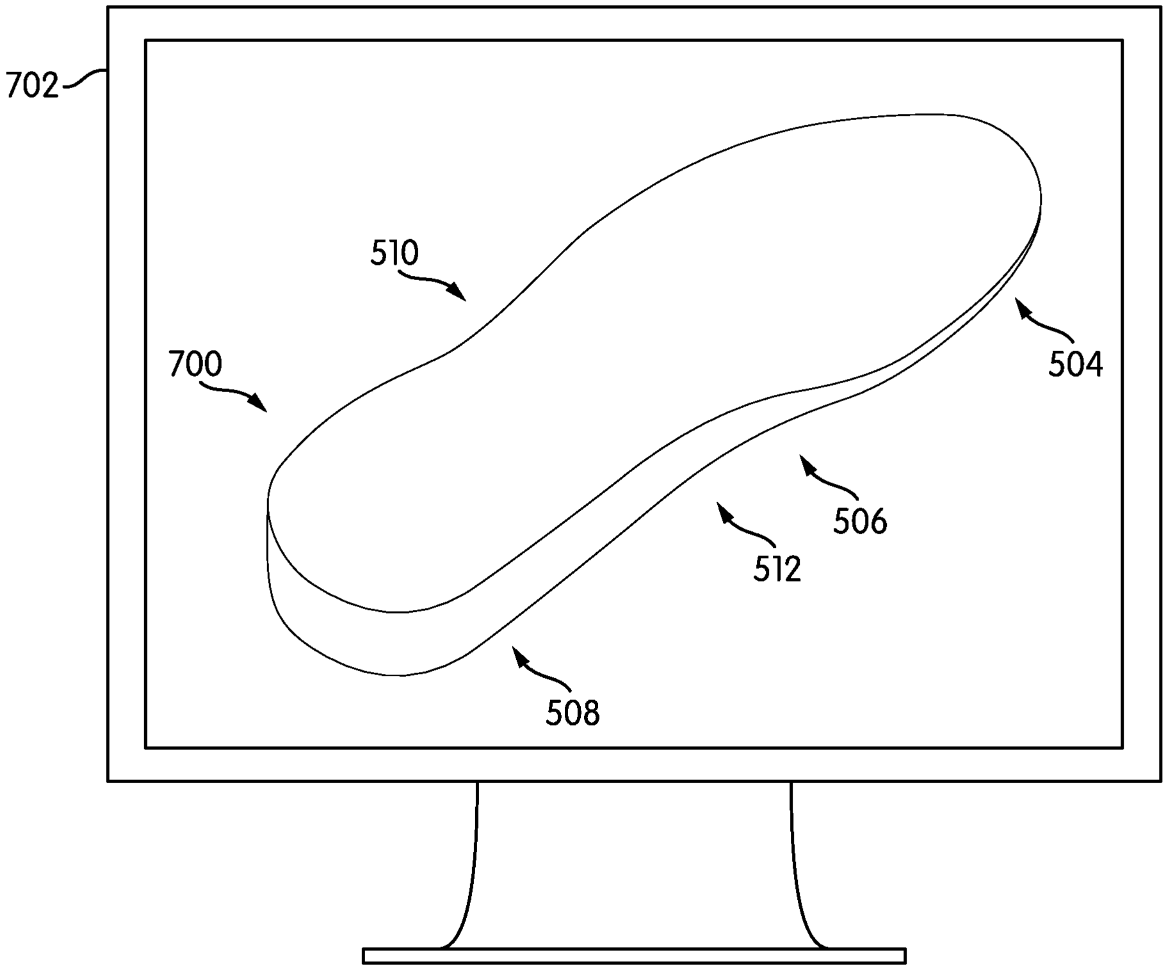
Figure 8:
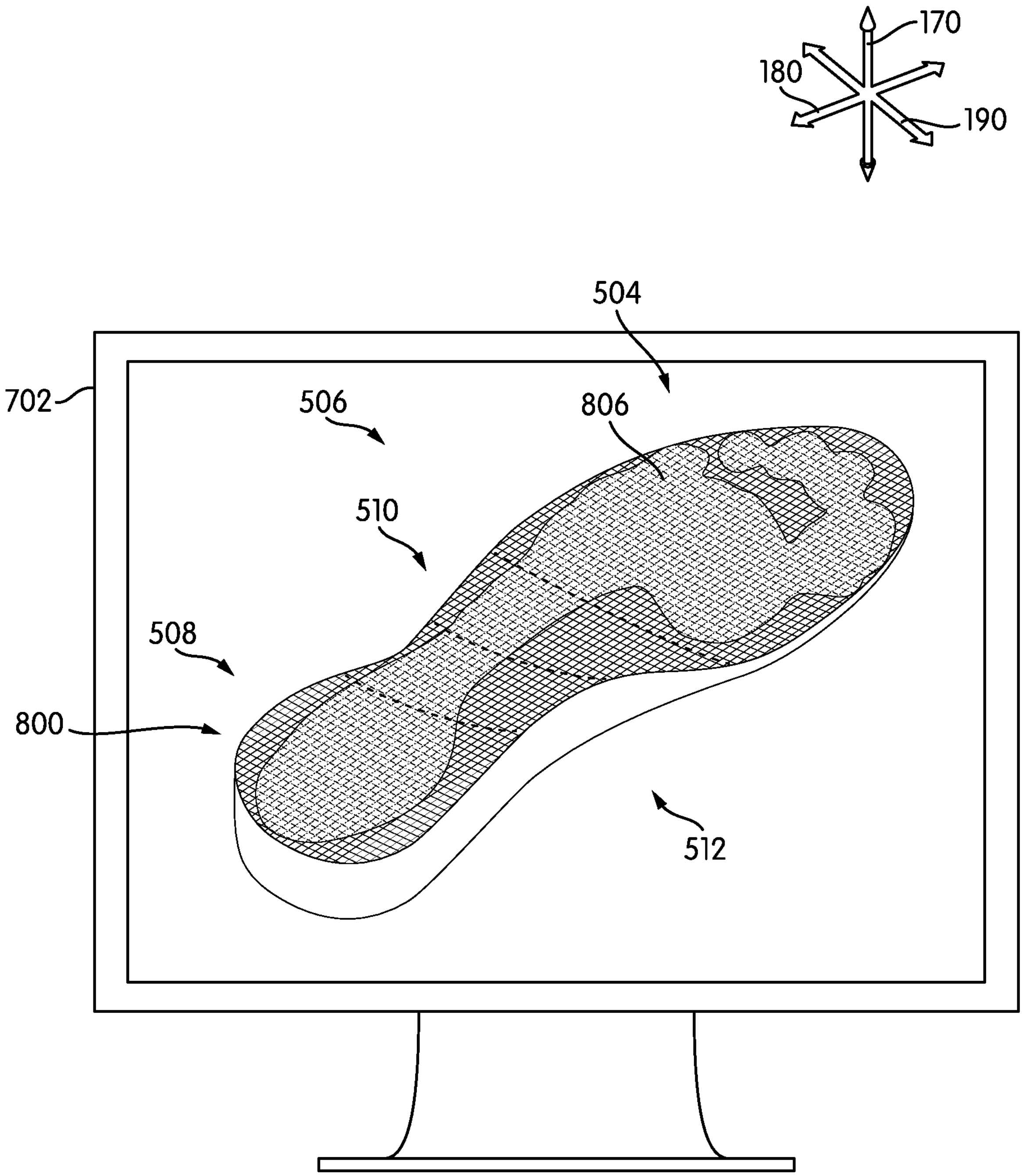
FIG. 8 schematically illustrates an embodiment of a virtual image of a customized sole member.

In different embodiments, a sole member may provide one or more functions for an article of footwear. In FIG. 7, an image of a template of a sole member 700 is displayed on a screen 702. In some embodiments, sole member 700 may attenuate ground reaction forces when compressed between the foot and the ground and/or an outsole during walking, running or other ambulatory activities. The configuration of sole member 700 may vary significantly in different embodiments to include a variety of conventional or non-conventional structures. In some cases, the configuration of sole member 700 can be selected or customized according to one or more types of ground surfaces on which sole member 700 may be used. Examples of ground surfaces include, but are not limited to: natural turf, synthetic turf, dirt, as well as other surfaces.

Upon obtaining measurements of foot 500 (see FIG. 5), sole member 700 may be adjusted or altered in different embodiments. As seen in the virtual representation depicted in FIG. 8, using the data collected from the steps above, a first custom sole 800 may be designed. In some embodiments, the design may utilize an application of an integrated computer aided design such as a computer automated manufacturing (CAD-CAM) process. Sole member 700, or any other template previously selected, may be provided as an input to the computer design program. In one embodiment, the three dimensional foot shape data from scan 600 in FIG. 6 is also provided to the program.

In different embodiments, scan 600 may provide information regarding foot shape and pressure to allow appropriate fit and comfort within the article of footwear. The information may be used to form first custom sole 800. In some embodiments, data from scan 600 may be superimposed or otherwise incorporated into the template of sole member 700 (see FIGS. 6 and 7). For example, there may be a process of aligning the data representing the plantar pressures of foot 500 with sole member 700 and generating a partial or complete design of first custom sole 800. In one embodiment, pressure contour lines 806 may be generated during design of first custom sole 800. The pressure distribution may be adjusted to a 'best-fit' position based upon user input in some embodiments. Once the distribution is finalized, a resiliency profile may be created. For purposes of this disclosure, a resiliency profile is a personalized pressure distribution for a user that may include the data collected during the steps described above. In some embodiments, the resiliency profile may be utilized in the production of first custom sole 800. Thus, in one embodiment, after the resiliency profile comprising an individual's plantar pressure distributions is aligned with the template of sole member 700, a customized sole member may be formed or manufactured.

It should be understood that, in different embodiments, the design of a sole member may include various modifications. Customized modifications may provide individual users with a wider range of comfort and fit. For example, different users may have differences in the height of the arch of foot 500. As described above, foot 500 may include multiple arches. Generally, the arch is a raised curve on the bottom surface of foot 500. When the tendons of foot 500 pull a normal amount, foot 500 generally forms a moderate or normal arch. However, when tendons do not pull together properly, there may be little or no arch. This is called "flat foot" or fallen arch. Over-pronation of a foot may be common for those with flat feet. The framework of a foot can collapse, causing the foot to flatten and adding stress to other parts of the foot. Individuals with flat feet may need orthotics to control the flattening of the foot. Moreover, the opposite may also occur, though high foot arches are less common than flat feet. Without adequate support, highly arched feet tend to be painful because more stress is placed on the section of the foot between the ankle and toes. This condition can make it difficult to fit into shoes. Individuals who have high arches usually need foot support. It should be noted that such variations in arch height are one of many possible examples of customized foot geometry that may be incorporated into a design.

Figure 9:
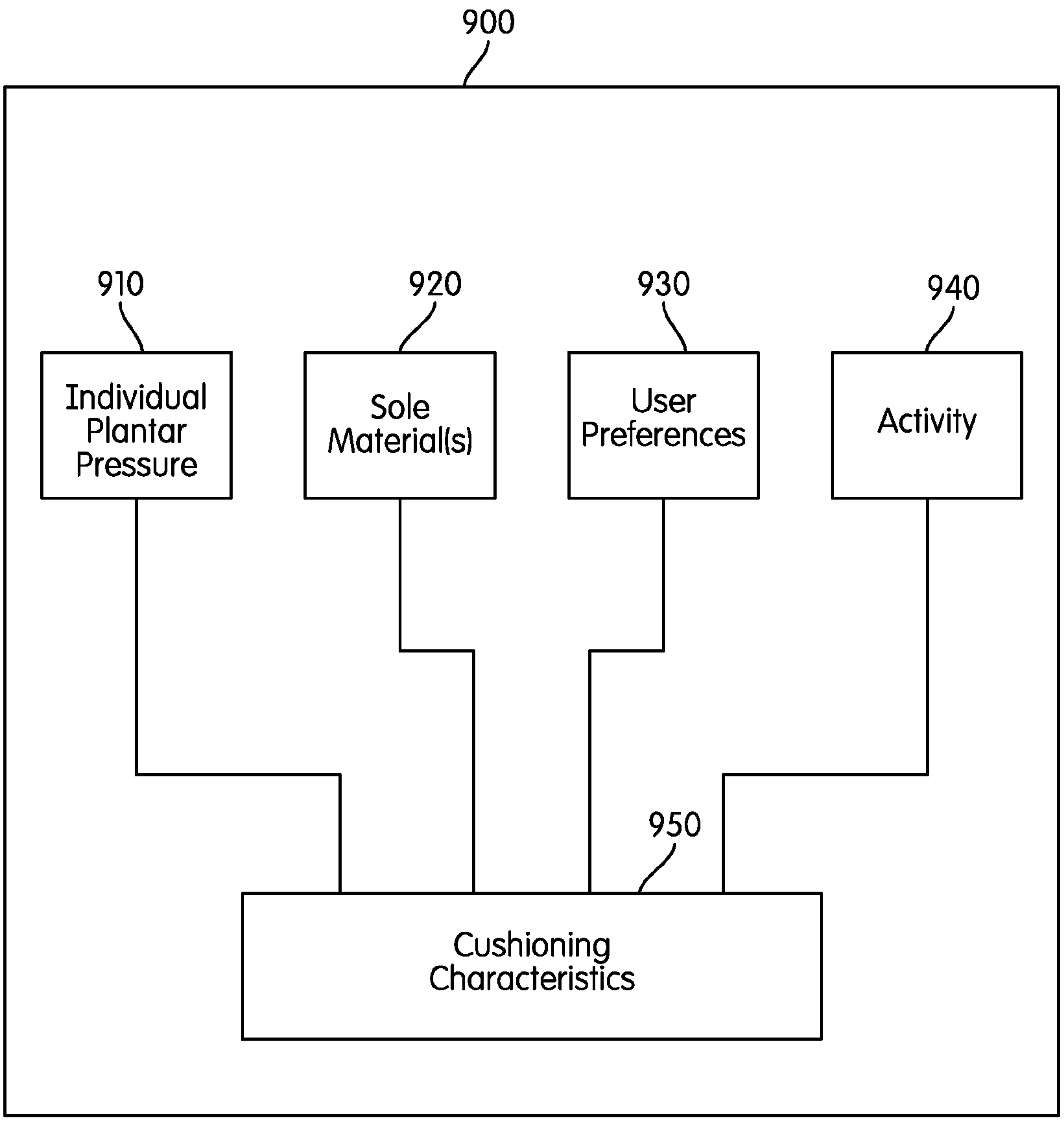
FIG. 9 is an embodiment of an influence diagram.

Referring to FIG. 9, an embodiment of an influence diagram 900 is depicted. Influence diagram 900 reflects some of the factors or variables that can be considered, incorporated, and/or used during the generation of the resiliency profile, permitting customization of cushioning characteristics 950 of a sole member. For example, a first factor 910 includes an individual's measured plantar pressure for each foot, which was discussed above with respect to FIG. 5-6. In addition, a second factor 920 may include the materials that will be used to form the custom sole member. A third factor 930 can be the individual user's own personal preferences regarding the type or level of cushioning desired. A fourth factor 940 may be the activity or sport that the user will be generally engaging in while using the custom sole member. In some cases, the sole member can be designed or tailored to provide special cushioning in areas or regions of the sole member that typically experience more force or pressure from the foot during specific activities. Thus, in some embodiments, one or more of these factors can contribute to cushioning characteristics 950 of a sole member. It should be understood that influence diagram 900 is provided as an example, and many other factors not listed here may be included in other embodiments. Furthermore, one or more factors listed in influence diagram 900 may be removed from consideration depending on the desired output or the goal of the custom sole member.

Once a design has been generated, as with first custom sole 800, the sole member may be manufactured. In some embodiments, the modifications may include regions of the sole member with apertures 150 disposed along different portions of the sole member. In some embodiments, a sole member can be molded in a manner that creates apertures in the sole member. An article of footwear including apertures can be formed in any manner. In some embodiments, apertures can be created in a sole member using any known methods of cutting or drilling. For example, in one embodiment, apertures can be created using laser cutting techniques. Specifically, in some cases, a laser can be used to remove material from a sole member in a manner that forms apertures in the sole member. In another embodiment, a hot knife process could be used for forming apertures in a sole member. Examples of methods for forming apertures on a sole member are disclosed in McDonald, U.S. Pat. No. 7,607,241, issued Oct. 27, 2009, titled "Article of Footwear with an Articulated Sole Structure," (previously U.S. patent application Ser. No. 11/869,604, filed Oct. 9, 2007), the entirety of which is hereby incorporated by reference. In other embodiments, however, any other type of cutting method can be used for forming apertures. Furthermore, in some cases, two or more different techniques can be used for forming apertures. As an example, in another embodiment, apertures disposed on a side surface of a sole member can be formed using laser cutting, while apertures on a lower surface of the sole member could be formed during a molding process. Still further, different types of techniques could be used according to the material used for a sole member. For example, laser cutting may be used in cases where the sole member is made of a foam material.

Figure 10:
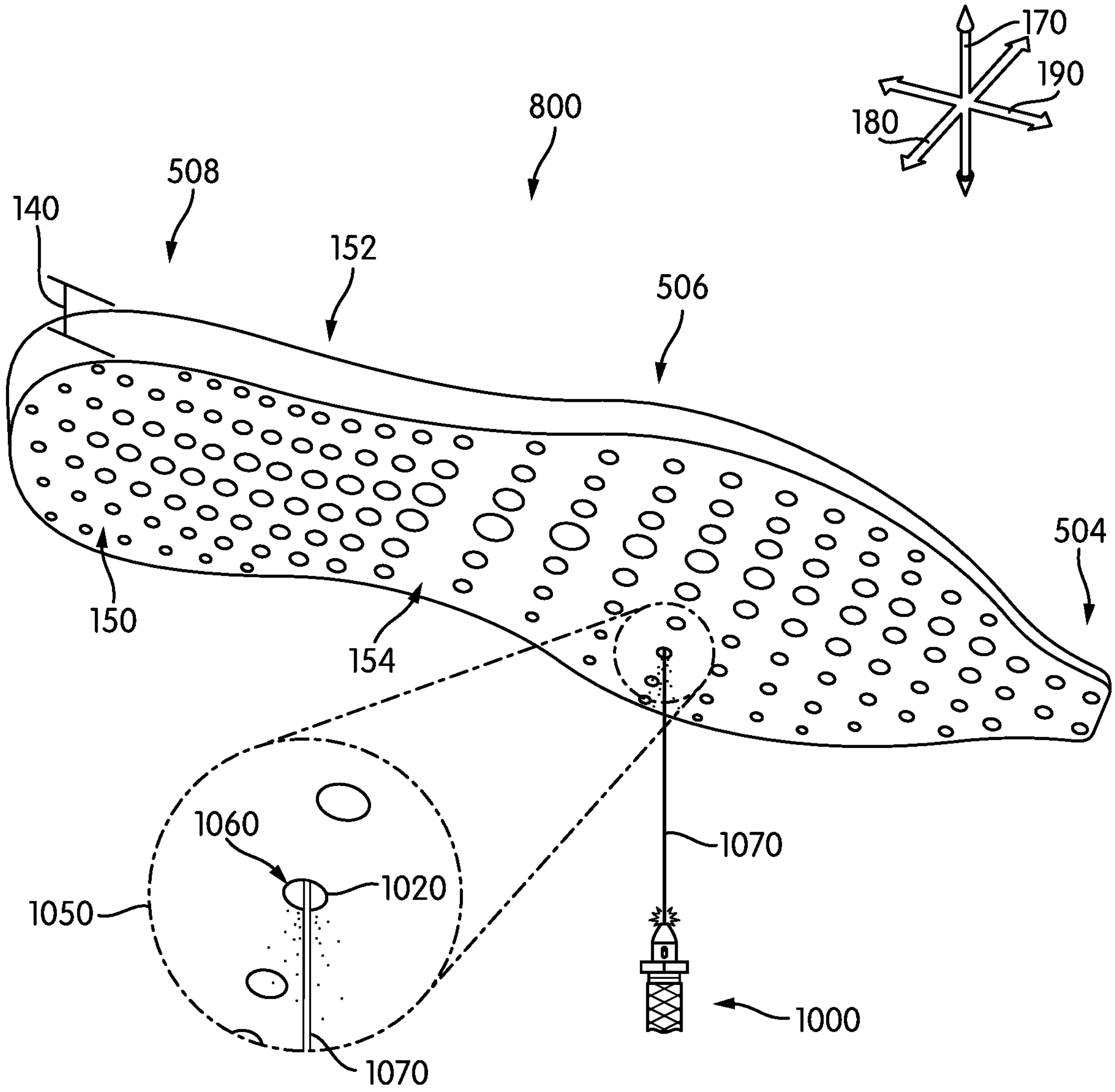
FIG. 10 is an isometric view of an embodiment of a sole member during a process of forming apertures.

In FIG. 10, a figure depicting an embodiment of a method of forming first custom sole 800, including apertures, is shown. Referring to FIG. 10, apertures 150 can be applied to or formed in first custom sole 800 using a laser drill 1000. In one embodiment, laser drill 1000 may be used to cut away or remove material through thickness 140 of first custom sole 800. In other cases, there may be a greater number of laser drills used. In FIG. 10, a group of apertures are being formed along lower surface 154 of first custom sole 800. It can be seen that apertures have also been previously formed by laser drill 1000.

Although only apertures over one surface are shown being drilled in this example, it will be understood that a similar method could be used for creating or forming apertures in any other region of first custom sole 800. It should further be understood that laser drill 1000 may include provisions for moving along different directions in order to direct the laser beam to the desired location. Furthermore, the sole member may be disposed such that it may be automatically or manually moved to receive a laser 1070 at the appropriate or desired location, such as along forefoot region 504, midfoot region 506, and/or heel region 508. In addition, while only one laser drill 1000 is shown in use in FIG. 10, in other embodiments, two, three, four or more laser drills may be engaged with the sole member.

In some embodiments, referring to a magnified area 1050, it can be seen that laser 1070 may contact lower surface 154 of first custom sole 800. When laser 1070 contacts the material, it may begin to remove material and form a hole 1020. As laser 1070 continues to engage with the material of the sole member, hole 1020 may grow through thickness 140 and form a first aperture 1060.

It may be recalled that each aperture may be formed such that they differ in one or more respects from one another, or they may be formed in a uniform manner, such that they are substantially similar in size, length, and shape. Furthermore, it should be understood that laser 1000 may be oriented at an angle different from that shown in FIG. 10, so that laser 1000 can form apertures 150 oriented in a diagonal or non-parallel manner with respect to vertical axis 170, longitudinal axis 180, and/or lateral axis 190.

Thus, as described herein, in some embodiments, the arrangement of apertures on a sole member could be varied to tune properties of the sole member for specific types of physical or personal characteristics, and/or athletic activities, and to provide a particular local cushioning characteristic. For example, in some cases, the arrangement of apertures on a sole member could be selected according to the type of sport for which the article of footwear is intended. In some embodiments, a manufacturer could vary the arrangement of apertures for various types of footwear, including, but not limited to, soccer footwear, running footwear, cross-training footwear, basketball footwear, as well as other types of footwear. Additionally, in other embodiments, the arrangement of apertures on a sole member could be varied according to the gender of the intended user. For example, in some cases, the aperture arrangements may vary between footwear for men and footwear for women. Still further, in some embodiments, the arrangement of apertures on a sole member could be varied according to preferences of a user for achieving desired performance effects. As an example, a desire for increased flexibility on a lateral side of the article can be accommodated by increasing the number and/or size of apertures on the lateral side of the sole member. In addition, in some embodiments, the configuration of apertures on a sole could be varied to achieve various visual or graphical effects. Furthermore, as discussed above, the arrangement of apertures can be individually customized by measuring various pressure regions of a person's foot and applying that information to the positioning and type of apertures on the sole member.

It should be understood that methods of customizing aperture configuration for particular sports, gender and/or personal preferences can be achieved in any manner. In one embodiment, a method of customizing aperture configuration for an article can include provisions for allowing a user to select a customized aperture arrangement by interacting with a website that provides customization tools for varying the number and/or geometry of various apertures. Examples of different customization systems that can be used for customizing aperture configurations are disclosed in Allen et al., U.S. Patent Publication Number 2005/0071242, published Mar. 31, 2005, titled "Method and System for Custom-Manufacturing Footwear," (previously U.S. patent application Ser. No. 10/675,237, filed Sep. 30, 2003), and Potter et al., U.S. Patent Publication Number 2004/0024645, published Feb. 5, 2004, titled "Custom Fit Sale of Footwear," (previously U.S. patent application Ser. No. 10/099,685, filed Mar. 14, 2002) the entirety of both being hereby disclosed by reference. It will be understood that the method of customizing aperture arrangements for an article of footwear are not limited to use with any particular customization system and in general any type of customization system known in the art could be used.

Articles of the embodiments discussed herein may be made from materials known in the art for making articles of footwear. For example, a sole member may be made from any suitable material, including, but not limited to: elastomers, siloxanes, natural rubber, other synthetic rubbers, aluminum, steel, natural leather, synthetic leather, foams or plastics. In an exemplary embodiment, materials for a sole member can be selected to enhance the overall flexibility, fit and stability of the article. In one embodiment, a foam material can be used with sole member, as foam can provide the desired elasticity and strength. In another embodiment, a rubber material could be used to make a midsole of a sole member. In still another embodiment, a thermoplastic material could be used with a sole member. For example, in one embodiment, thermoplastic polyurethane (TPU) may be used to make a midsole for a sole member. In still other embodiments, a sole member may comprise a multi-density insert that comprises at least two regions of differing densities. For example, in one other embodiment, a midsole of a sole member could be configured to receive one or more inserts. Examples of different types of inserts that could be used are disclosed in Yu et al., U.S. Pat. No. 7,941,938, issued May 17, 2011, titled "Article of Footwear with Lightweight Sole Assembly," (previously U.S. patent application Ser. No. 11/752,348, filed Mar. 23, 2007) the entirety of which is hereby incorporated by reference. Also, an upper may be made from any suitable material known in the art, including, but not limited to: nylon, natural leather, synthetic leather, natural rubber or synthetic rubber.

An article of footwear can include provisions for adjusting the flexibility characteristics of a sole member with a plurality of apertures. In some embodiments, different materials can be used with different portions of a sole. In an exemplary embodiment, portions of a sole can be filled with additional material or components to provide different types of cushioning, feel, and flexibility for a sole member. For example, in one embodiment, a core portion of a sole member may comprise a fluid filled member, such as an air bladder. In another embodiment, one or more portions of a sole member could include hollow cavities capable of receiving fluid or other materials.

Thus, as described herein, in some embodiments, the arrangement of apertures on a sole structure could be varied to tune properties of the sole structure for specific types of athletic activities. For example, in some cases, the arrangement of apertures on a sole structure could be selected according to the type of sport for which the article of footwear is intended. In some embodiments, a manufacturer could vary the arrangement of apertures for various types of footwear, including, but not limited to, soccer footwear, running footwear, cross-training footwear, basketball footwear, as well as other types of footwear. Additionally, in other embodiments, the arrangement of apertures on a sole structure could be varied according to the gender of the intended user. For example, in some cases, the aperture arrangements may vary between footwear for men and footwear for women. Still further, in some embodiments, the arrangement of apertures on a sole structure could be varied according to preferences of a user for achieving desired performance effects. As an example, a desire for increased flexibility on a lateral side of the article can be accommodated by increasing the number and/or geometry of apertures on the lateral side of the sole structure. In addition, in some embodiments, the configuration of apertures on a sole could be varied to achieve various visual or graphical effects. Furthermore, as discussed above, the arrangement of apertures can be individually customized by measuring various pressure regions of a person's foot and applying that information to the positioning and type of apertures on the sole structure.

It should be understood that methods of customizing aperture configuration for particular sports, gender and/or personal preferences can be achieved in any manner. In one embodiment, a method of customizing aperture configuration for an article can include provisions for allowing a user to select a customized aperture arrangement by interacting with a website that provides customization tools for varying the number and/or geometry of various apertures. Examples of different customization systems that can be used for customizing aperture configurations are disclosed in U.S. Patent Application Publication Number 2005/0071242, to Allen, and U.S. Patent Application Publication Number 2004/0024645, to Potter et al., the entirety of both being hereby disclosed by reference. It will be understood that the method of customizing aperture arrangements for an article of footwear are not limited to use with any particular customization system and in general any type of customization system known in the art could be used.

An article of footwear can include provisions for adjusting the flexibility characteristics of a sole structure with a plurality of apertures. In some embodiments, different materials can be used with different portions of a sole. In an exemplary embodiment, portions of a sole can be filled with additional material or components to provide different types of cushioning, feel, and flexibility for a sole structure. For example, in one embodiment, a core portion of a sole structure may comprise a fluid filled member, such as an air bladder. In another embodiment, one or more portions of a sole structure could include hollow cavities capable of receiving fluid or other materials.

Figure 11:
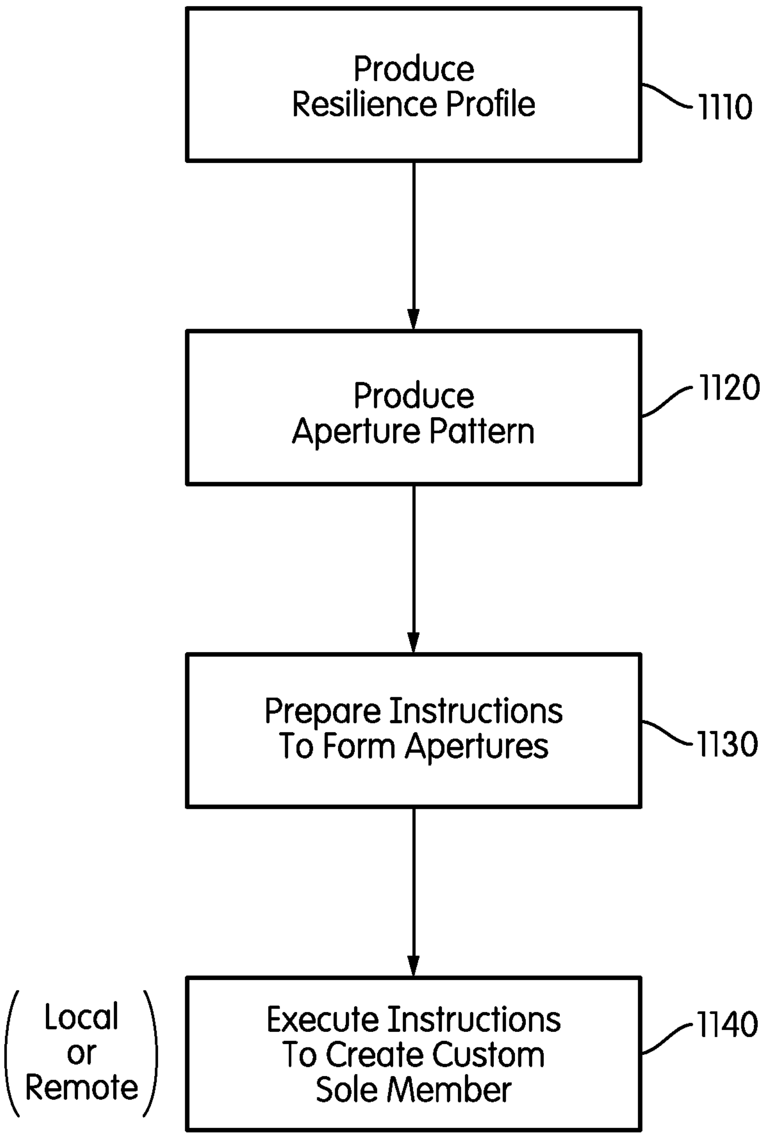
FIG. 11 is an embodiment of a flow chart for a method of making a custom sole member.

An embodiment of the sole member production process as described herein is outlined in the flow chart of FIG. 11. In a first step 1110, a pressure distribution of a user's feet is obtained (see FIGS. 5-8 above). In other words, the pressure distributions associated with a user's left foot and/or a right foot (i.e., a first foot and a second foot) may be obtained. The pressure distributions as well as any other preferences are collected to generate a resiliency profile. In a second step 1120, the resiliency profile may be used to produce a custom configuration or pattern of apertures (e.g., position, size, lengths, orientation, etc.) in a sole member. The particular configuration of apertures generated may be stored in a virtual or digital form in some embodiments. It should be understood that in some embodiments, a first pattern of apertures may be produced for a left foot, and a second pattern of apertures may be produced for a corresponding right foot. Following the production of one or more aperture patterns, instructions to form the apertures in a sole member may be prepared or generated in a third step 1130. In some cases, the aperture pattern may be converted into a series of commands or instructions for a system to follow in order to translate the aperture pattern into mechanical or design steps for forming the customized sole member. Finally, in a fourth step 1140, the instructions are executed and a custom sole member is produced. In some embodiments, the instructions may be executed to produce a first custom sole member (e.g., for a left foot) and a complementary second custom sole member (e.g., for a right foot).

The process described herein may occur in rapid succession and in close proximity to one another in some embodiments. However, in other embodiments, one or more steps may occur spaced apart in time and location. In other words, one step may occur in a first location, and another step may occur in a second location, where the first location is different from the second location. For example, the resiliency profile of first step 1110 may be produced off-site (e.g., at a shopping outlet or a medial office, etc.), and the aperture pattern of second step 1120 may be produced in a manufacturing facility. In another example, the instructions for forming the apertures of third step 1130 may be prepared or generated in a local site, while the actual production of the custom sole member of fourth step 1140 may occur in a remote site (e.g., out of state, or abroad).

Figure 12:
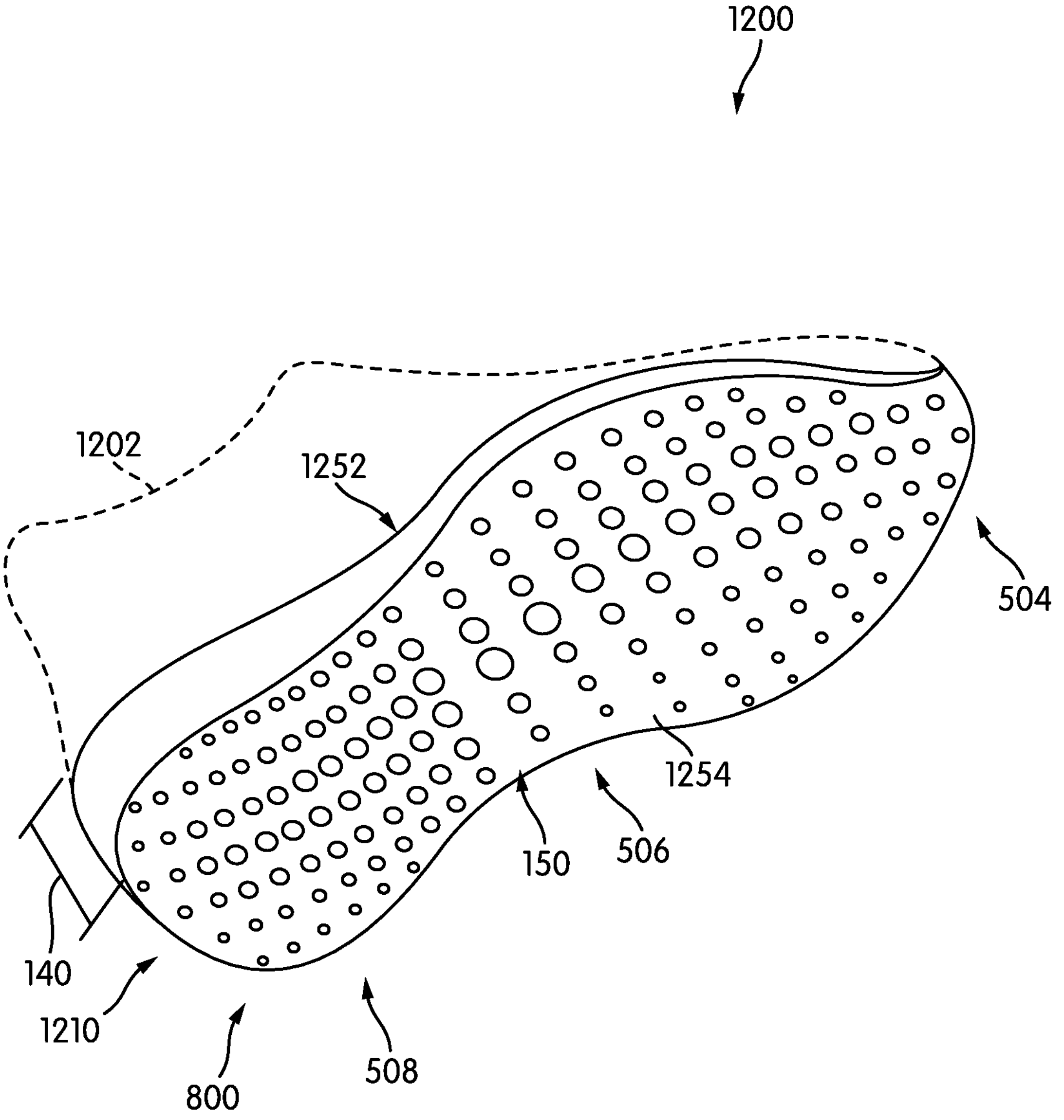
FIG. 12 is an isometric bottom view of an embodiment of a sole member.

FIG. 12 illustrates another embodiment of a custom sole member for an article of footwear. In FIG. 12, an article of footwear 1200 is shown, hereby referred to as article 1200. Article of footwear 1200 can be configured as any type of footwear including, but not limited to: hiking boots, soccer shoes, football shoes, sneakers, rugby shoes, basketball shoes, baseball shoes as well as other kinds of footwear. Article 1200 can comprise an upper 1202 and a sole structure 1210. Sole structure 1210 is secured to upper 1202 and extends between the foot and the ground or an outsole when article 1200 is worn. In different embodiments, sole structure 1210 may include different components. For example, sole structure 1210 may include an outsole, a midsole, and/or an insole. In some cases, one or more of these components may be optional.

Generally, a customized sole member may comprise any layer or element of sole structure 1210, and be configured as desired. In particular, layers of the sole structure may have any design, shape, size and/or color. For example, in embodiments where an article of footwear is a basketball shoe, a sole member could include contours shaped to provide greater support to heel prominence. In embodiments where the article of footwear is a running shoe, the custom sole member could be configured with contours supporting forefoot region 504. In some embodiments, sole structure 1210 could further include provisions for fastening to an upper or another sole layer, and may include still other provisions found in footwear sole members. Also, some embodiments of sole structure 1210 may include other materials disposed within the custom sole member, such as air bladders, leather, synthetic materials (such as plastic or synthetic leather), mesh, foam, or a combination thereon.

The material selected for sole structure 1210 or components of sole structure 1210 may possess sufficient durability to withstand the repetitive compressive and bending forces that are generated during running or other athletic activities. In some embodiments, the material(s) may include foams, polymers such as urethane or nylon; resins; metals such as aluminum, titanium, stainless steel, or lightweight alloys; or composite materials that combine carbon or glass fibers with a polymer material, ABS plastics, PLA, glass filled polyamides, stereolithography materials (epoxy resins), silver, titanium, steel, wax, photopolymers and polycarbonate. The customized sole member may also be formed from a single material or a combination of different materials. For example, one side of a custom sole member may be formed from a polymer whereas the opposing side may be formed from a foam. In addition, specific regions may be formed from different materials depending upon the anticipated forces experienced by each region.

Referring to FIG. 12, an embodiment of completed first custom sole 800 in an article of footwear 1200 is shown. Upper 1202 is attached to first custom sole 800. As shown in FIG. 12, first custom sole 800 includes apertures 150 of varying sizes arranged throughout lower surface of first custom sole 800 in regions that may generally correspond to the regions of foot 500 that were indicated to have increased plantar pressures (see FIGS. 5 and 6). In other words, the plantar pressure distribution comprising pressure contour lines 806 (see FIG. 8) can be generally aligned with the disposition of apertures 150 in first custom sole 800. Thus, in one embodiment, first pressure area 604, second pressure area 606, third pressure area 608, fourth pressure area 610, and/or fifth pressure area 612 (see FIG. 6) can be accommodated by or correspond to different sets of apertures 150 formed in first custom sole 800.

Depending on the magnitude of the measured plantar pressures, apertures in each area can be larger or more numerous. In other words, in areas of the foot associated with higher plantar pressures, the number and/or size of apertures may be increased. For example, in some embodiments, the plantar pressure associated with heel region 508 may be largest. In such embodiments, there can be larger apertures disposed in heel region 508 relative to other regions of first custom sole 800. In another embodiment, the plantar pressure associated with midfoot region 506 and/or forefoot region 504 can be greatest. Thus, there may be larger apertures disposed on midfoot region 506 and/or forefoot region 504.

Depending on the magnitude of the measured plantar pressures, apertures in each area can be larger or more numerous. In other words, in areas of the foot associated with higher plantar pressures, the number and/or size of apertures may be increased. For example, in some embodiments, the plantar pressure associated with heel region 508 may be largest. In such embodiments, there can be larger apertures disposed in heel region 508 relative to other regions of first custom sole 800.

Thus, in some embodiments, custom sole members as described herein can decrease the plantar pressures acting beneath the forefoot region 504, midfoot region 506, and/or heel region 508, and may help offload areas of higher pressures. A more appropriate type and amount of cushioning can be generated for a user using the embodiments depicted herein, reducing the amount of pressure experienced by foot 500. For example, if plantar pressure values are determined to be atypical, the information can be used to modify a person's footwear (i.e., the sole member) to provide the person with footwear more effective in producing a more typical pattern of foot loading during walking or other activities.

In FIG. 12, an upper surface 1252 is provided on the upper side of first custom sole 800, and a lower surface 1254 is provided on the bottom side (i.e., the side that would be facing the ground when worn by a user). Together, upper surface 1252 and lower surface 1254 comprise an exterior surface of first custom sole 800. Disposed along various portions of the exterior surface are apertures 150 that extend varying lengths and comprising varying patterns through thickness 140 (i.e., within an interior portion) of first custom sole 800. In some embodiments, apertures 150 may be disposed on both upper surface 1252 and lower surface 1254 of first custom sole 800. In other embodiments, apertures 150 may be disposed on only one surface of first custom sole 800. In FIG. 12, apertures 150 are formed along lower surface 1254. More details regarding this embodiment are provided in FIGS. 13-15 below.

Figure 13:
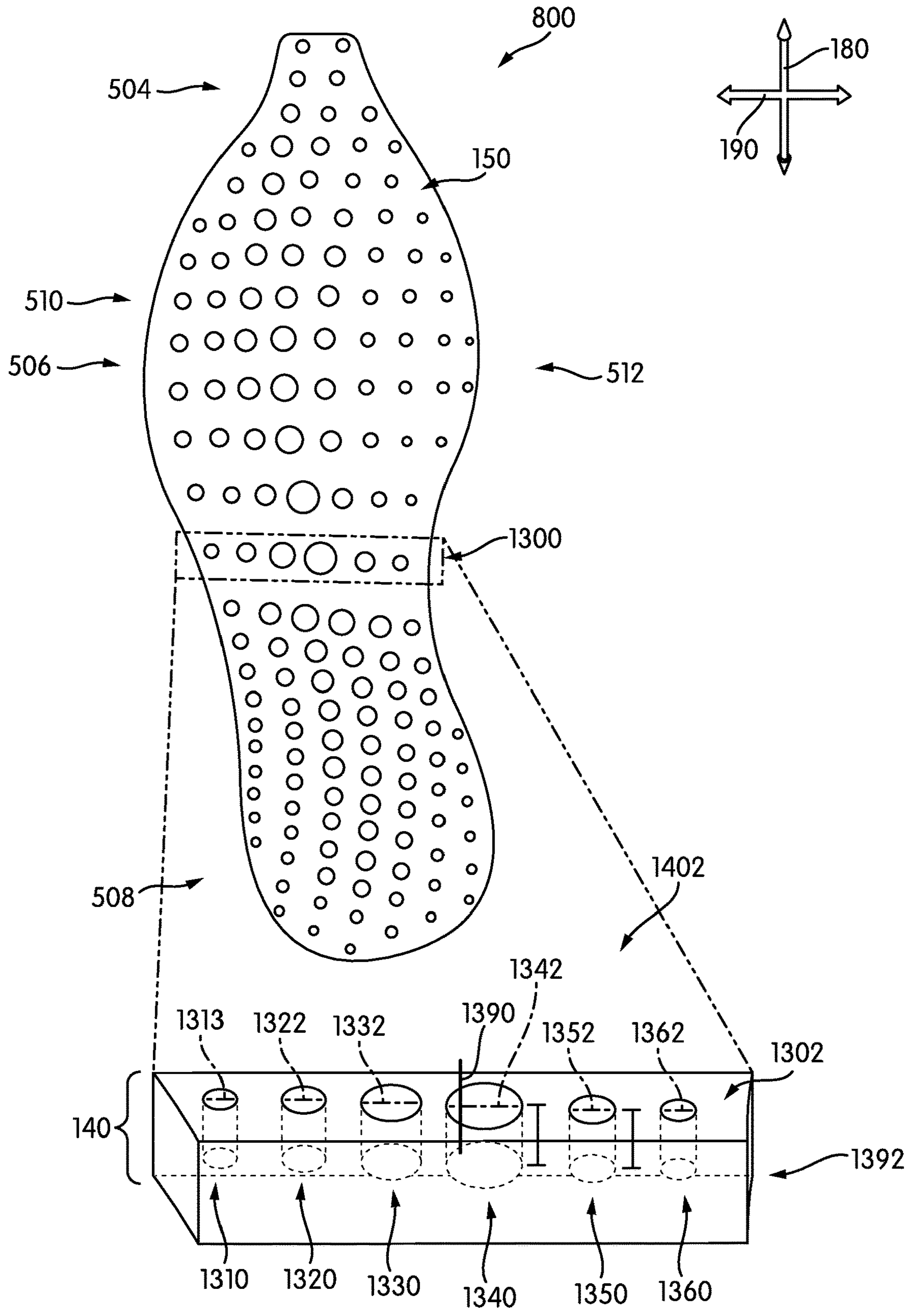
FIG. 13 is a bottom view of an embodiment of a sole member.
Figure 14:
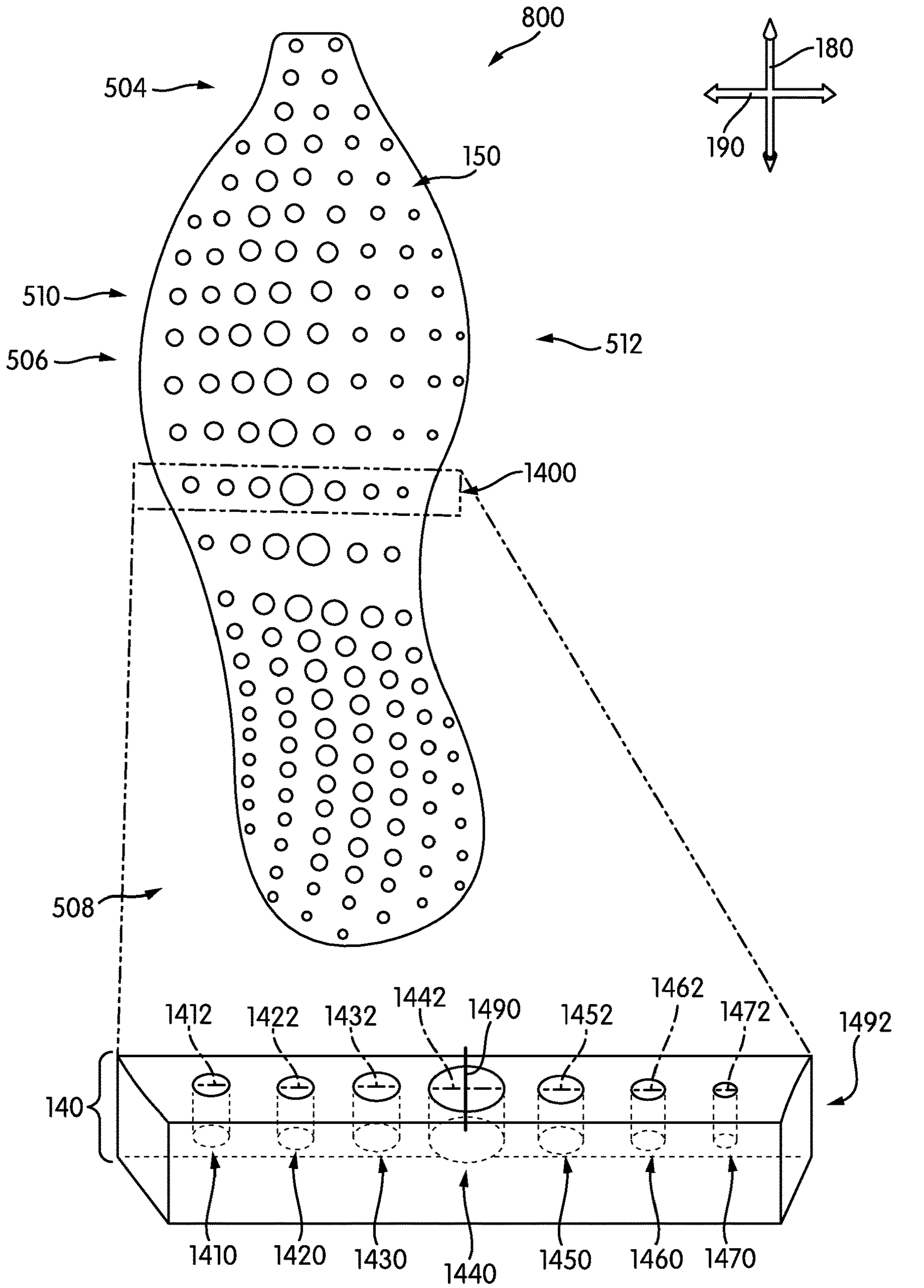
FIG. 14 is a bottom view of an embodiment of a sole member.
Figure 15:
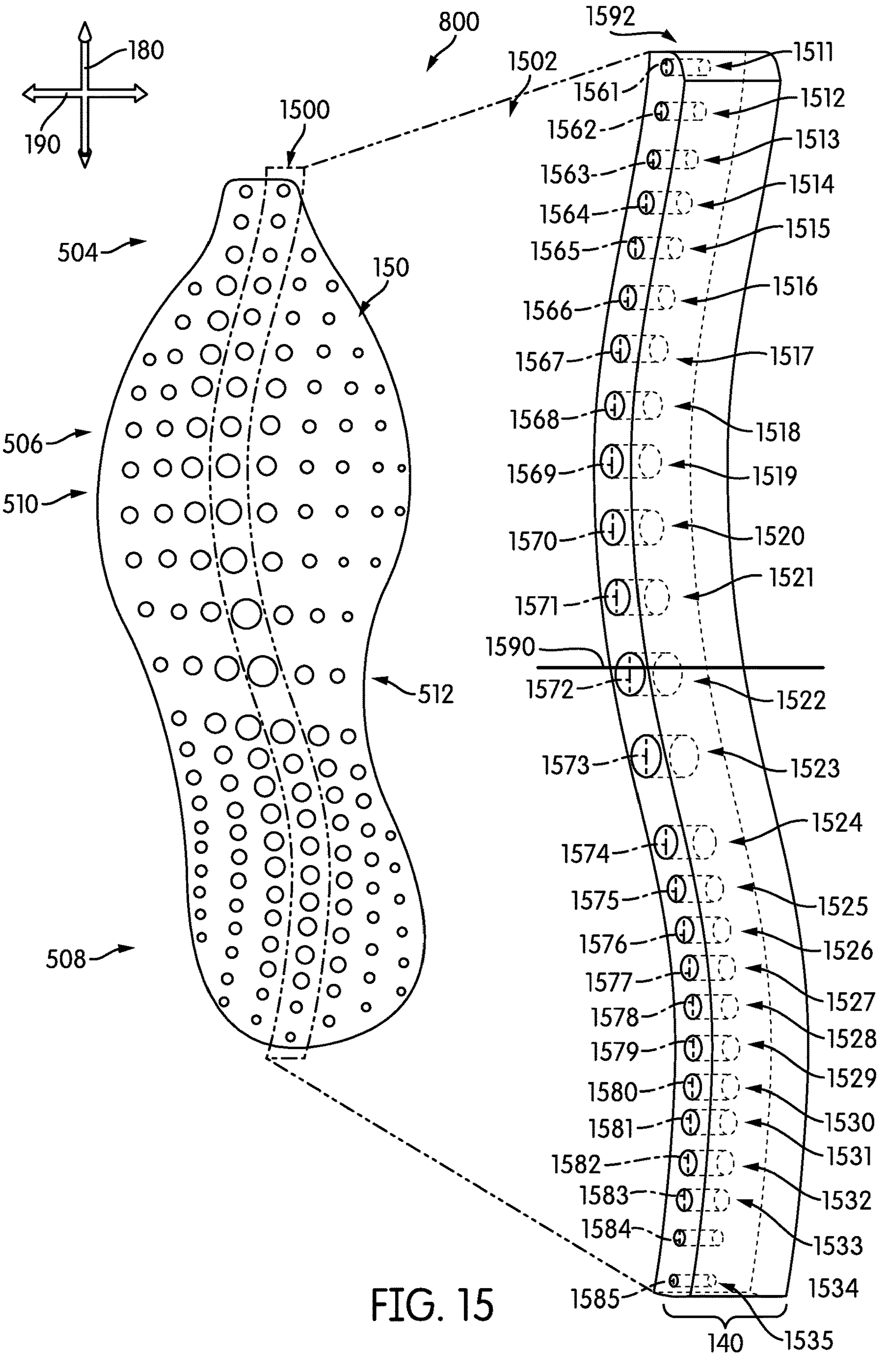
FIG. 15 is a bottom view of an embodiment of a sole member.

FIGS. 13-15 provide a series of illustrations of an embodiment of lower surface 1254 of first custom sole 800 for an article of footwear. Referring to FIG. 13, a first portion 1300 of first custom sole 800 comprising a first set of apertures ("first set") 1302 is shown in an isometric first cutaway view 1392. First portion 1300 comprises a portion of first custom sole 800 that extends from lateral side 510 to medial side 512. In first set 1302, as best seen in first cutaway view 1392, there are six apertures arranged across substantially the entire lateral width of first portion 1300, including a first aperture 1310, a second aperture 1320, a third aperture 1330, a fourth aperture 1340, a fifth aperture 1350, and a sixth aperture 1360. The six apertures comprising first set 1302 are arranged such that they are generally aligned along the direction of lateral axis 190.

As noted above, in different embodiments, two or more apertures 150 may include extend through thickness 140 with varying lengths. In some embodiments, the apertures of first set 1302 can extend through thickness 140 with varying lengths along vertical axis 170. For example, fourth aperture 1340 has a length that is greater than the length of fifth aperture 1350. The lengths of each aperture can differ from one another, or two or more apertures may have substantially similar lengths. The lengths of the apertures may be selected to provide specific cushioning characteristics.

Furthermore, apertures may comprise varying sizes in different embodiments. In other words, the average cross-sectional size of each aperture can be smaller or larger than a neighboring aperture. For example, in the embodiment of FIG. 13, each of the apertures of first set 1302 are associated with a different size relative to one another. Thus, first aperture 1310 has a first size 1313, second aperture 1320 has a second size 1322, third aperture 1330 has a third size 1332, fourth aperture 1340 has a fourth size 1342, fifth aperture 1350 has a fifth size 1352, and sixth aperture 1360 has a sixth size 1362. For reference purposes, the sizes identified are associated with the diameter of the aperture; however, in other embodiments, sizes may be measured by other parameters, such as interior volume, perimeter, and/or area.

The magnitude of each aperture size may increase in one direction and/or decrease in another direction in some embodiments. In other words, there may be a pattern formed in the sole member related to the size of the adjacent apertures along a direction aligned with lateral axis 190. In one embodiment, shown in FIG. 13, as apertures of first set 1302 approach a first midline 1390 from lateral side 510, the size of each aperture can increase. In addition, as apertures approach first midline 1390 from medial side 512, the size of each aperture can increase. As shown in first set 1302, first size 1313 is smaller than second size 1322, second size 1322 is smaller than third size 1332, and third size 1332 is smaller than fourth size 1342. Furthermore, sixth size 1362 is smaller than fifth size 1352, and fifth size 1352 is smaller than fourth size 1342. Thus, in some cases, the sizes of apertures may oscillate, undulate, taper, fade, or otherwise form a type of pattern. In some embodiments, apertures may generally decrease in size as they approach first midline 1390. In one embodiment, apertures may generally increase in size from lateral side 510 to medial side 512. In another embodiment, the apertures may generally decrease in size from lateral side 510 to medial side 512. It should be understood that references to a midline in this disclosure is for reference purposes only and the midline may be proximate a center or generally near a center of the sole members.

Furthermore, it should be understood that in other embodiments, two or more apertures may have diameters or sizes that are substantially similar to one another. For example, first size 1313 and sixth size 1362 may be substantially equivalent. In other cases, all apertures of first set 1302 may have similar sizes. Furthermore, in another embodiment, the apertures may have sizes that are irregular with respect to one another, such that no appreciable pattern is formed.

In some embodiments, a different pattern may be formed. Referring to FIG. 14, a second portion 1400 of first custom sole 800 comprising a second set of apertures ("second set") 1402 is shown in an isometric second cutaway view 1492. Second portion 1400 comprises a portion of first custom sole 800 that extends from lateral side 510 to medial side 512, similar to first portion 1300 identified in FIG. 13. In second set 1402, as best seen in second cutaway view 1492, there are seven apertures, including a first aperture 1410, a second aperture 1420, a third aperture 1430, a fourth aperture 1440, a fifth aperture 1450, a sixth aperture 1460, and a seventh aperture 1470. The seven apertures comprising second set 1402 are arranged such that they are generally aligned with lateral axis 190.

As described with respect to FIG. 13, apertures may comprise varying sizes in different embodiments. In other words, the overall or average cross-sectional size of each aperture can be smaller or larger than a neighboring aperture. For example, in the embodiment of FIG. 14, several of the apertures of second set 1402 are associated with a different size relative to one another. First aperture 1410 has a first size 1412, second aperture 1420 has a second size 1422, third aperture 1430 has a third size 1432, fourth aperture 1440 has a fourth size 1442, fifth aperture 1450 has a fifth size 1452, sixth aperture 1460 has a sixth size 1462, and seventh aperture 1470 has a seventh size 1472. For reference purposes, the sizes identified are associated with the diameter of the aperture; however, in other embodiments, sizes may be measured by other parameters, such as interior volume, perimeter, and/or area.

The magnitude of each aperture size may increase in one direction and/or decrease in another direction in some embodiments. In other words, there may be a pattern formed in the sole member related to the size of the adjacent apertures. In one embodiment, shown in FIG. 14, as apertures of second set 1402 approach a second midline 1490 from medial side 512, the size of each aperture can increase. As shown in second set 1402, seventh size 1472 is smaller than sixth size 1462, sixth size 1462 is smaller than fifth size 1452, and fifth size 1452 is smaller than fourth size 1442. Fourth size 1442 may be significantly larger than neighboring apertures in second set 1402 in some embodiments.

However, it should be understood that in other embodiments, two or more apertures may have diameters or sizes that are substantially similar to one another. For example, first size 1412 and second size 1422 are substantially equivalent in FIG. 14. In other cases, one or more apertures of second set 1402 disposed on medial side 512 relative to first midline 1390 may have similar sizes. In another embodiment, one or more apertures of second set 1402 disposed on lateral side 510 relative to first midline 1390 may have similar sizes.

In some embodiments, there may be apertures formed in directions aligned with other orientations or have a different arrangement. In FIG. 15, a third portion 1500 is depicted an isometric third cutaway view 1592. Third portion 1500 has a third set of apertures ("third set") 1502 disposed over substantially the entire longitudinal length of lower surface 1254 of third portion 1500, extending from forefoot region 504 to heel region 508.

Specifically referring to FIG. 15, in third set 1502 (as best seen in third cutaway view 1592), there are 25 apertures, including a first aperture 1511, a second aperture 1512, a third aperture 1513, a fourth aperture 1514, a fifth aperture 1515, a sixth aperture 1516, a seventh aperture 1517, an eighth aperture 1518, a ninth aperture 1519, a tenth aperture 1520, an eleventh aperture 1521, a twelfth aperture 1522, a thirteenth aperture 1523, a fourteenth aperture 1524, a fifteenth aperture 1525, a sixteenth aperture 1526, a seventeenth aperture 1527, an eighteenth aperture 1528, a nineteenth aperture 1529, a twentieth aperture 1530, a twenty-first aperture 1531, a twenty-second aperture 1532, a twenty-third aperture 1533, a twenty-fourth aperture 1534, and a twenty-fifth aperture 1535. The 25 apertures comprising third set 1502 are arranged such that they are generally extending in the direction associated with longitudinal axis 180.

Furthermore, apertures may comprise varying sizes in different embodiments. In other words, the overall or average cross-sectional size of each aperture can be smaller or larger than a neighboring aperture. For example, in the embodiment of FIG. 15, several of the apertures of third set 1502 are associated with a different size relative to one another. Thus, first aperture 1511 has a first size 1561, second aperture 1512 has a second size 1562, third aperture 1513 has a third size 1563, fourth aperture 1514 has a fourth size 1564, fifth aperture 1515 has a fifth size 1565, sixth aperture 1516 has a sixth size 1566, seventh aperture 1517 has a seventh size 1567, eighth aperture 1518 has an eighth size 1568, ninth aperture 1519 has a ninth size 1569, tenth aperture 1520 has a tenth size 1570, eleventh aperture 1521 has an eleventh size 1571, twelfth aperture 1522 has a twelfth size 1572, and thirteenth aperture 1523 has a thirteenth size 1573. In addition, fourteenth aperture 1524 has a fourteenth size 1574, fifteenth aperture 1525 has a fifteenth size 1575, sixteenth aperture 1526 has a sixteenth size 1576, seventeenth aperture 1527 has a seventeenth size 1577, eighteenth aperture 1528 has an eighteenth size 1578, nineteenth aperture 1529 has a nineteenth size 1579, twentieth aperture 1530 has a twentieth size 1580, twenty-first aperture 1531 has a twenty-first size 1581, twenty-second aperture 1532 has a twenty-second size 1582, twenty-third aperture 1533 has a twenty-third size 1583, twenty-fourth aperture 1534 has a twenty-fourth size 1584, and twenty-fifth aperture 1535 has a twenty-fifth size 1585. For reference purposes, the sizes identified are associated with the diameter of the aperture; however, in other embodiments, sizes may be measured by other parameters, such as interior volume, perimeter, and/or area.

As seen in FIG. 15, at least some of the apertures in third set 1502 are arranged in a generally oscillating pattern, such that the size of each aperture gradually increases as the apertures approach a third midline 1590, and then decrease or taper toward zero as the apertures approach an edge. As noted above, apertures 150 may be arranged in a geometric pattern to provide a wearer with enhanced or improved support and cushioning, and such an oscillating pattern may improve the comfort and feel of the sole member for a foot.

In other words, the magnitude of each aperture size may increase in one direction and/or decrease in another direction in some embodiments. Thus, there may be a pattern formed in the sole member in a direction generally aligned with longitudinal axis 180 based on the cross-sectional size of the adjacent apertures. In other embodiments, there may be a curvature (i.e., non-linear) to the arrangement of a column of apertures that extend from heel region 508 to forefoot region 504. Thus, the use of the label "column" should be understood to refer to an arrangement of apertures that that are adjacent to one another in a general direction extending from heel region 508 to forefoot region 504, rather than necessarily being aligned in a straight or undeviating arrangement.

In one embodiment, shown in FIG. 15, as apertures of third set 1502 approach second midline 1390 from heel region 508, the size of each aperture can increase. In addition, as apertures approach third midline 1590 from forefoot region 504, the size of each aperture can increase.

Some examples of different patterns can be seen in FIG. 15. As shown in third set 1502, beginning in forefoot region 504, fifth size 1565 is smaller than sixth size 1566, sixth size 1566 is smaller than seventh size 1567, seventh size 1567 is smaller than eighth size 1568, eighth size 1568 is smaller than ninth size 1569, and ninth size 1569 is smaller than tenth size 1570. Similarly, beginning in heel region 508, twenty-fifth size 1585 is smaller than twenty-fourth size 1584, twenty-fourth size 1584 is smaller than twenty-third size 1583, and twenty-third size 1583 is smaller than twenty-second size 1582. In addition, fifteenth size 1575 is smaller than fourteenth size 1574, and fourteenth size 1574 is smaller than thirteenth size 1573.

Thus, in some embodiments, the sizes of apertures may oscillate, undulate, taper, fade, or otherwise form a type of pattern. In other embodiments, apertures may generally decrease in size as they approach third midline 1590. In one embodiment, apertures may generally increase in size from forefoot region 504 to heel region 508. In another embodiment, the apertures may generally decrease in size from forefoot region 504 to heel region 508.

However, it should be understood that in other embodiments, two or more apertures may have diameters or sizes that are substantially similar to one another. For example, twenty-first size 1581, twentieth size 1580, nineteenth size 1579, eighteenth size 1578, seventeenth size 1577, and sixteenth size 1576 may be substantially equivalent. In other cases, all apertures of third set 1502 may have similar sizes. In other embodiments, two or more apertures of third set 1502 disposed toward heel region 508 relative to third midline 1590 may have similar sizes. In another embodiment, two or more apertures of third set 1502 disposed toward forefoot region 504 relative to third midline 1590 may have similar sizes.

Furthermore, in another embodiment, the apertures may have sizes that are irregular with respect to one another, such that no appreciable pattern is formed. In other words, at least some of the apertures in third set 1502 can be arranged in an irregular fashion with respect to aperture size.

As noted above, aperture depths and/or sizes may be configured to perform specialized or customized support and cushioning. Thus, the sizes of apertures 150 may be selected and/or formed to provide customized support for an individual foot. In different embodiments, as shown in FIGS. 13-15, first custom sole 800 can provide both generalized cushioning, as well as specialized (i.e., uniquely tailored) cushioning.

Figure 16:
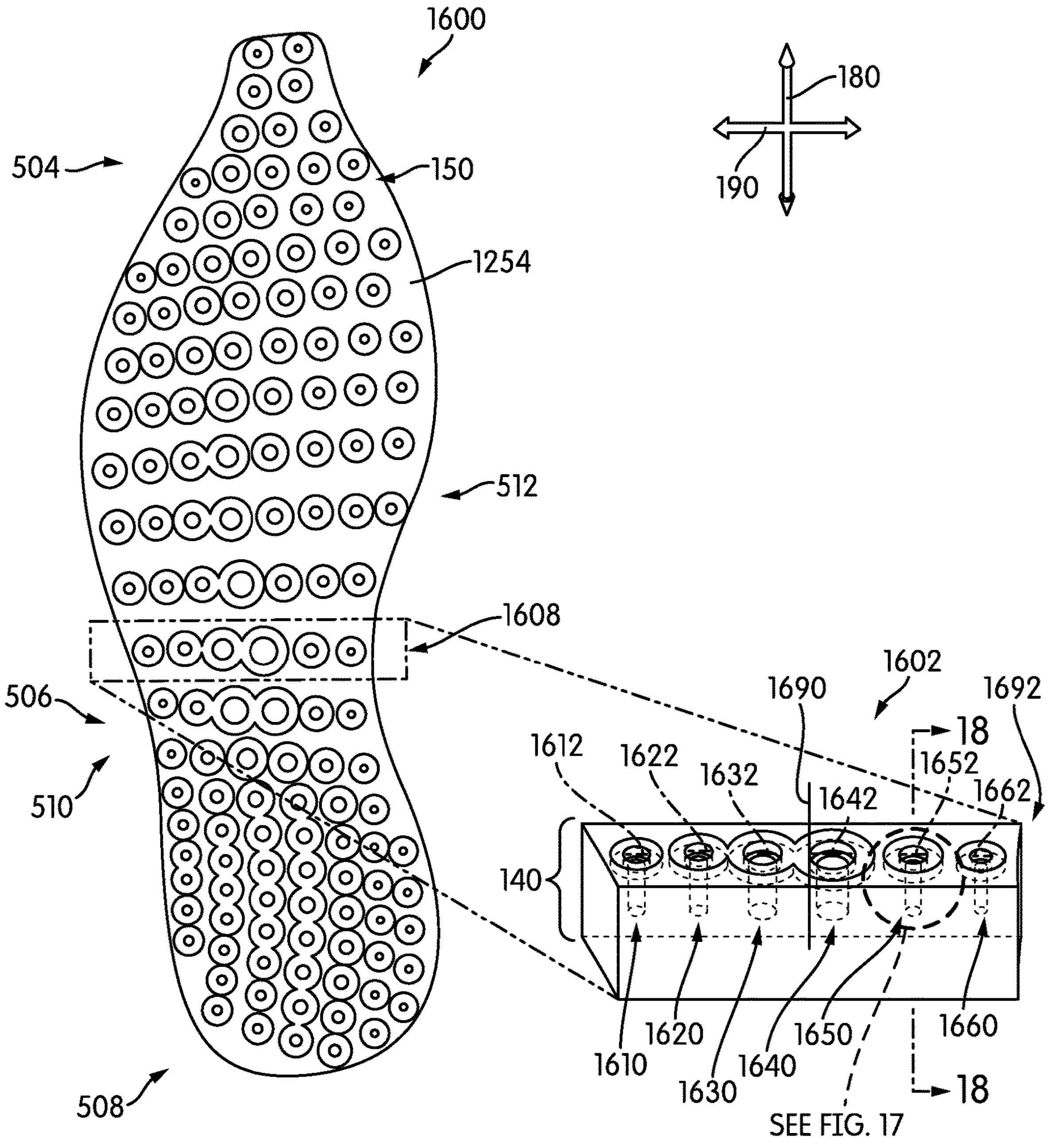
FIG. 16 is a bottom view of an embodiment of a sole member.

FIG. 16 illustrates an embodiment of lower surface 1254 of a second custom sole 1600. Referring to FIG. 16, a fourth portion 1608 of second custom sole 1600 comprising a fourth set of apertures ("fourth set") 1602 is shown in an isometric fourth cutaway view 1692. Fourth portion 1608 comprises a portion of second custom sole 1600 that generally extends from lateral side 510 to medial side 512. In the example provided by fourth set 1602 (as best seen in fourth cutaway view 1692), there are six apertures arranged across substantially the entire lateral width of fourth portion 1608 including a first aperture 1610, a second aperture 1620, a third aperture 1630, a fourth aperture 1640, a fifth aperture 1650, and a sixth aperture 1660. Similar to the embodiment of first set 1302 in FIG. 13, the six apertures comprising fourth set 1602 in FIG. 16 are arranged in a direction generally aligned with lateral axis 190.

Furthermore, apertures may comprise varying sizes in different embodiments. In other words, the overall or average cross-sectional size of each aperture can be smaller or larger than a neighboring aperture. For example, in the embodiment of FIG. 16, several of the apertures of fourth set 1602 are associated with a different size relative to one another. In FIG. 16, first aperture 1610 has a first size 1612, second aperture 1620 has a second size 1622, third aperture 1630 has a third size 1632, fourth aperture 1640 has a fourth size 1642, fifth aperture 1650 has a fifth size 1652, and sixth aperture 1660 has a sixth size 1662.

As described with respect to FIGS. 13-15, the magnitude of each aperture size may increase in one direction and/or decrease in another direction in some embodiments. In other words, there may be a pattern formed in the sole member related to the size of the adjacent apertures in a direction generally aligned with lateral axis 190 and/or longitudinal axis 180. For example, as apertures of fourth set 1602 approach a fourth midline 1690 from lateral side 510, the size of each aperture can increase. In addition, as apertures approach fourth midline 1690 from medial side 512, the size of each aperture can increase. As shown in fourth set 1602, first size 1612 is smaller than second size 1622, second size 1622 is smaller than third size 1632, and third size 1632 is smaller than fourth size 1642. Furthermore, sixth size 1662 is smaller than fifth size 1652, and fifth size 1652 is smaller than fourth size 1642. Thus, in some cases, the sizes of apertures may oscillate, undulate, taper, fade, or otherwise form a type of pattern. In some embodiments, apertures may generally decrease in size as they approach fourth midline 1690. In one embodiment, apertures may generally increase in size from lateral side 510 to medial side 512. In another embodiment, the apertures may generally decrease in size from lateral side 510 to medial side 512.

However, it should be understood that in other embodiments, two or more apertures may have diameters or sizes that are substantially similar to one another. For example, second size 1622 and fifth size 1652 may be substantially equivalent. In other cases, all apertures of fourth set 1602 may have similar sizes. Furthermore, in another embodiment, the apertures may have sizes that are irregular with respect to one another, such that no appreciable pattern is formed.

In addition, two or more apertures may be disposed at different distances from one another. For example, in one embodiment, first aperture 1610 is disposed such that it is distinct and separate from second aperture 1620. However, third aperture 1630 and fourth aperture 1640 are disposed such that they adjoin one another, and have merged boundaries. In other words, two apertures can approach, touch and/or merge with one another. Thus, in some embodiments, two or more apertures may be disposed close enough to one another so as to form a substantially continuous opening similar to a siping. In some embodiments, the distance between two apertures may be approximately zero. In different embodiments, a feature similar to a siping can be a result of the varying degrees of merging between adjoining apertures. In some embodiments, apertures may be formed in various portions of a cushioning element to create a siping-like region, groove, or channel, through the cushioning element. While the arrangement can provide variations in cushioning, there may be other benefits, including enhanced traction or grip of the exterior surface. Various designs or flexible regions may also be formed by the inclusion of such siped apertures.

Furthermore, as noted above, in different embodiments, apertures 150 may extend through thickness 140 with varying lengths or depths. In the embodiment of FIG. 16, fourth portion 1608 includes apertures that extend through thickness 140 with depths that vary in a vertical direction relative to other apertures. However, in some embodiments, there may be differences in depth within a single aperture. In other words, a single aperture may include a "step", or different level portions that are associated with different depths. For example, referring to FIG. 17, an isolated view of the portion of second custom sole 1600 that includes fifth aperture 1650 is illustrated. Fifth aperture 1650 can be seen to include a first portion 1710 and a second portion 1720. First portion 1720 has a base 1750 that extends a first distance from lower surface 1254, where the first distance can vary in length. In addition, there is a smaller sub-aperture 1770 disposed within base 1750 that is associated with second portion 1720. Sub-aperture 1770 can extend various depths through the interior portion of second custom sole 1600.

Figure 17:
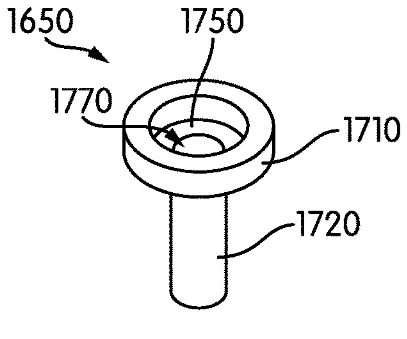
FIG. 17 is a cross-section of an embodiment of a portion of a sole member.
Figure 18:
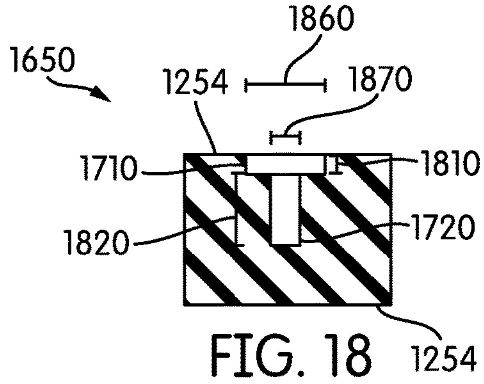
FIG. 18 is an embodiment of a portion of an aperture in a sole member.

Referring now to FIG. 18, a cross-section of fifth aperture 1650 is depicted. It can be seen that fifth aperture 1650 has a first depth 1810 associated with first portion 1710, and a second depth 1820 associated with second portion 1720. In some embodiments, first depth 1810 may be more shallow (i.e., less deep) than second depth 1820. In FIG. 17, first depth 1810 forms an outer boundary or ledge (similar to a step) between second depth 1820 and lower surface 1254. For purposes of this disclosure, fifth aperture 1650 may be referred to as including two "levels", where each level is associated with the different depth provided within the aperture. It should be understood that first depth 1810 may be greater than, less than, or substantially similar to second depth 1820 in different embodiments. In FIG. 18, first depth 1810 is less than second depth 1820.

Thus, in some embodiments, apertures may include various depth levels within a single aperture. In other embodiments, fifth aperture 1650 may include multiple depth levels, beyond those illustrated in FIGS. 16-18. For example, fifth aperture 1650 may include three, four, or five levels.

It should be understood that, in some embodiments, each level may also include a corresponding cross-sectional size that differs from the cross-sectional size of an adjacent level. For example, referring again to fifth aperture 1650 in FIG. 18, first portion 1710 can be associated with first size 1860, and second portion 1720 can be associated with a second size 1870. In different embodiments, first size 1860 may be greater than, less than, or substantially similar to second size 1870. In FIG. 18, first size 1860 is greater than second size 1870.

In some embodiments, apertures 150 may be arranged to form regular rows along first custom sole 800. As shown in FIG. 12-16, there are 25 rows of apertures, and eight columns of apertures. In other embodiments, there may be less than or greater than 25 rows, and/or less than or greater than eight columns. For purposes of this disclosure, rows and/or columns need not be linear, and may comprise curving areas where the neighboring apertures in a column or row are generally aligned but may be offset from one another. For example, first set 1302 comprises a row of apertures, and third set 1502 comprises a column of apertures. Each row and column can include a different number of apertures than shown here (i.e., more than or less than 6 rows and/or more than or less than 25 columns).

In different embodiments, each size of the apertures may be similar or may differ from that depicted here. For example, in other embodiments, first aperture 1310 may be larger than fourth aperture 1340. Thus, in some embodiments, apertures 150 disposed on first custom sole 800 can have varying sizes with respect to one another, or they may have the same size. Furthermore, apertures 150 may vary with respect to one another in shape, or the shapes may each be the same. In other embodiments, apertures 150 may differ from one another in both size and shape along the same surface.

Figure 19:
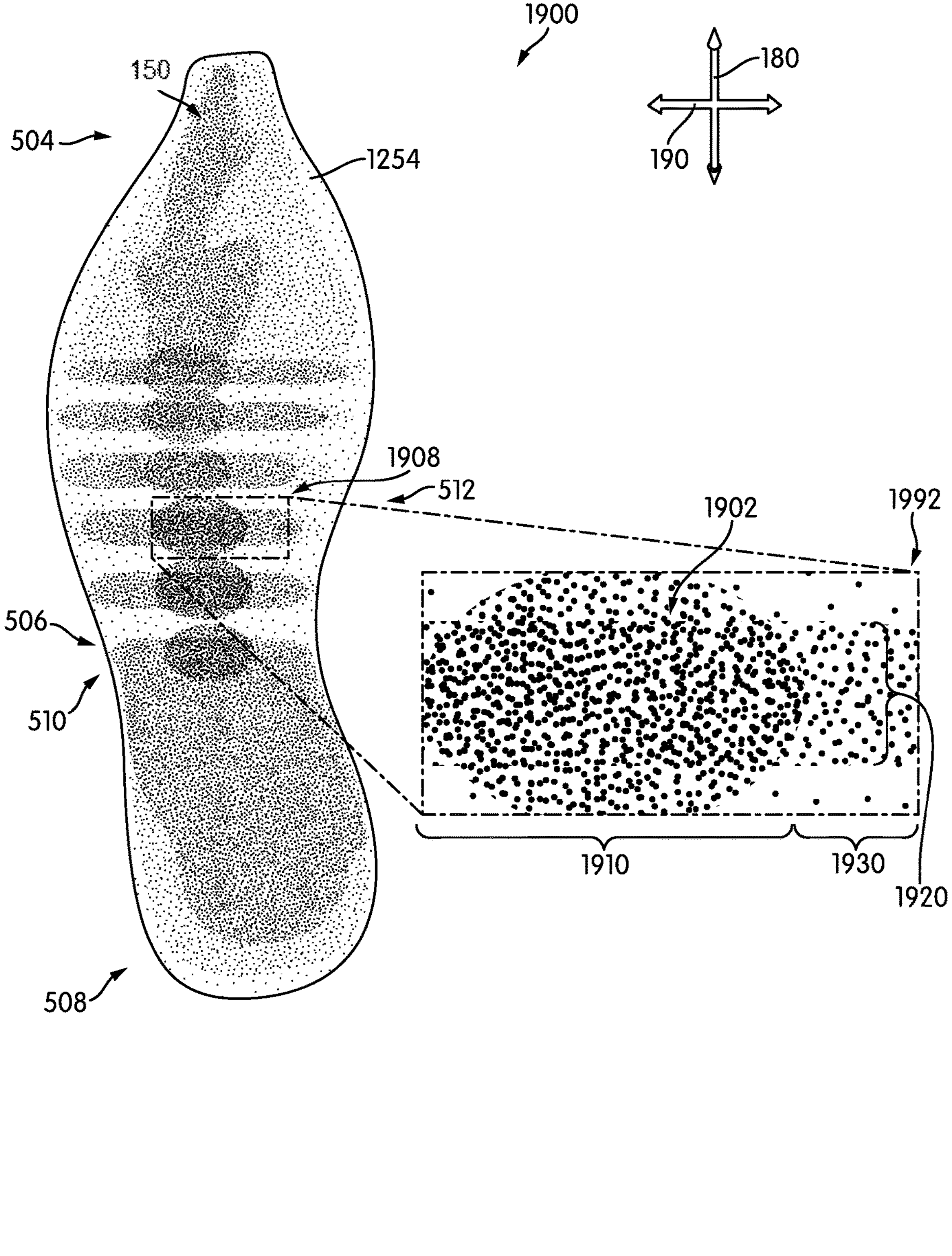
FIG. 19 is a bottom view of an embodiment of a sole member.

FIG. 19 illustrates an embodiment of lower surface 1254 of a third custom sole 1900. Referring to FIG. 19, a fifth portion 1908 of third custom sole 1900 comprising a fifth set of apertures ("fifth set") 1902 is shown in a magnified view 1992. Fifth portion 1908 comprises a portion of third custom sole 1900 that generally extends from lateral side 510 to medial side 512. In the example provided by fifth set 1902 (as best seen in magnified view 1992), there are a plurality of apertures arranged across substantially the entire lateral width of fifth portion 1908. The apertures are disposed at varying density distributions, including a first distribution 1910, a second distribution 1920, and a third distribution 1930. For purposes of this disclosure, density distribution, or distribution, refers to the average population of apertures per unit area or unit volume of the cushioning element. In other words, regions of third custom sole 1900 with a higher density will have a greater number of apertures disposed closer together than regions with a lower density. In some embodiments, apertures disposed more proximate to a longitudinal midline of the sole member may be generally arranged more closer together (i.e., in a more dense distribution) than apertures disposed further away from the longitudinal midline.

In different embodiments, as noted above, two or more apertures may be disposed at different distances from one another. For example, in one embodiment, apertures in the region associated with first distribution 1910 may be disposed on average more proximate to one another than apertures in the region associated with second distribution 1920. Furthermore, apertures in the region associated with second distribution 1920 may be disposed on average more proximate to one another than apertures in the region associated with third distribution 1930.

In different embodiments, one or more of the apertures described with respect to FIG. 19 may vary in size. In some embodiments at least some of the apertures may be smaller relative to the apertures of the embodiments described with respect to FIGS. 12-18. Thus, in some embodiments, one or more apertures may be between 0 and 5 millimeters in diameter. In other embodiments, one or more apertures may be between 0 and 2 millimeters in diameter. In one embodiment, a majority of the apertures may be less than 2 millimeters in diameter. In some cases, a majority or all of the apertures may be less than 1 millimeter in diameter. In other words, one or more apertures may be a "pinpoint" size in some embodiments, such that the depth and/or diameter of the aperture is very small relative to the sole member outer surface area.

In some embodiments, two or more apertures may be disposed such that they adjoin one another, and have merged boundaries. In other words, two apertures can approach, touch and/or merge with one another. Thus, in some embodiments, two or more apertures may be disposed close enough to one another so as to form a substantially continuous opening similar to a siping. In different embodiments, a siping facsimile can be a result of the varying degrees of merging between adjoining apertures. In some embodiments, the distance between two apertures may be approximately zero. In some embodiments, apertures may be formed in various portions of a cushioning element to create a siping-like region, groove, or channel, through the cushioning element. While the arrangement can provide variations in cushioning, there may be other benefits, including enhanced traction or grip of the exterior surface. Various designs or flexible regions may also be formed by the inclusion of such siped apertures. Thus, referring to third custom sole 1900, apertures may be disposed along various regions or portions of the sole such that varying distribution patterns are formed. In some embodiments, cushioning characteristics may be adjusted or customized based on the density of apertures included in different areas of third custom sole 1900.

As discussed in FIGS. 12-19, it can be seen that the number of apertures included in a sole member can vary. In some embodiments, apertures can comprise between 5% and 20% of lower surface 1254 of a sole member. In other embodiments, apertures can comprise between 10% and 30% of lower surface 1254 of a sole member. In different embodiments, apertures can comprise between 15% and 50% of lower surface 1254 of a sole member. In one embodiment, apertures can comprise over 50% of lower surface 1254 of a sole member.

Specifically referring to the illustrative embodiments of FIGS. 12-15, it can be seen that in some cases, apertures 150 can comprise at least 15% of lower surface 1254 of first custom sole 800. In FIG. 16, it can be seen that in other cases apertures 150 can comprise at least 30% of lower surface 1254 of second custom sole 1600. Furthermore, referring to FIG. 19, in some cases apertures 150 can comprise at least 45% of lower surface 1254 of third custom sole 1900.

Thus, the various cushioning elements as described here can provide a custom sole member with specialized responses to ground reaction forces. In one embodiment, the cushioning element may attenuate and distributes ground reaction forces. For example, when a portion of the custom sole member contacts the ground, the apertures disposed in cushioning element can help attenuate the ground reaction forces. The cushioning element may have the capacity to distribute the ground reaction forces throughout a substantial portion of the custom sole member. The attenuating property of this type of structure can reduce the degree of the effect that ground reaction forces have on the foot, and the distributive property distributes the ground reaction forces to various portions of a foot. In some embodiments, such features may reduce the peak ground reaction force experienced by the foot.

In other embodiments, the cushioning element designs disclosed in this description may also include provisions to achieve a non-uniform ground reaction force distribution. For example, the ground reaction force distribution of a custom sole member could provide a wearer with a response similar to that of barefoot running, but with attenuated ground reaction forces. That is, the custom sole member could be designed to impart the feeling of barefoot running, but with a reduced level of ground reaction forces. Additionally, in another example, the ground reaction forces could be more concentrated in the medial side of a foot than along a lateral side of a foot, thereby reducing the probability that the foot will over-pronate, or imparting greater resistance to eversion and inversion of the foot.

In some embodiments, the use of cushioning elements in orthotics for an article of footwear can help support weakened areas of the foot and assist the user in each step. While a relatively rigid material, as may be included in a custom sole member, can provide functional support to the foot, softer or more flexible regions associated with apertures can absorb the loads put on the foot and provide protection. Such softer or cushioned regions can better absorb the loads placed on a foot, increase stabilization, and take pressure off uncomfortable or sore spots of the feet.

Other embodiments or variations of custom sole members may include other lattice structure designs or various combinations of the above-disclosed designs. It should be noted that the present description is not limited to cushioning elements having the geometry or aperture configurations of first custom sole 800, second custom sole 1600, and third custom sole 1900. In different embodiments, each customized sole member may include further variations not depicted in the figures. Some variations may include differences in shape, size, contour, elevations, depressions, curvatures, and other variations. In other words, the custom sole members depicted herein are merely intended to provide an example of the many types of cushioning element-based sole member configurations that fall within the scope of the present discussion.

In different embodiments, sole members as well as any apertures in the sole members discussed herein may be formed using any other method known in the art. In some embodiments, any removal process (i.e., where a portion of a material is removed, subtracted, eliminated, etc.) may be used to form one or more apertures (e.g., apertures 150). For example, in some embodiments, a mechanical process may be used, including but not limited to ultrasonic machining, water jet machining, abrasive jet machining, abrasive water jet machining, ice jet machining, and/or magnetic abrasive finishing. In other embodiments, chemical processes may be utilized, including but not limited to chemical milling, photochemical milling, and/or eletropolishing. Furthermore, in some embodiments, electrochemical processes may be used. In other embodiments, thermal processes can be used, such as electrodischarge machining (EDM), laser beam machining, electron beam machining, plasma beam machining, and/or ion beam machining, or other processes. In another embodiment, hybrid electrochemical processes can be utilized, including but not limited to electrochemical grinding, electrochemical honing, electrochemical superfinishing, and/or electrochemical buffing. In addition, hybrid thermal processes may be used, such as electroerosion dissolution machining. In other embodiments, the material comprising the sole member may be modified using chemical processes, including temperature changes (e.g., freezing the material). Furthermore, the processes for forming the apertures may be applied or utilized after the article of footwear has been assembled, or the sole member has been associated with an upper or sole structure. In other words, the formation of apertures in a sole member may occur post-manufacturing of the article of footwear.

It should be understood that in other embodiments, the midsole can include a casing in a molded foam. In other words, embodiments of the sole member as described herein may be associated with the midsole of a sole structure. Thus, in some embodiments, a midsole may include a foam material. The foam material can comprise a 'skin' surface that is formed from a molding process. In some embodiments, the various removal processes described above (e.g., drilling, laser, chemical, EDM, water cutting, etc.) can be applied to the foam skin of a midsole and apertures can be formed in a manner similar to the embodiments discussed above.

While various embodiments have been described, the description is intended to be exemplary, rather than limiting and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A sole structure for an article of footwear, the sole structure comprising:
- a sole member, the sole member including an outer surface, the outer surface comprising an upper surface and a lower surface;
- the sole member having a set of pinpoint apertures, wherein each aperture of the set of pinpoint apertures is a blind-hole aperture, and wherein a majority of apertures of the set of pinpoint apertures have a diameter less than 1 mm;
- wherein the set of pinpoint apertures are disposed along the outer surface of the sole member to form at least a first distribution of apertures and a second distribution of apertures; and
- wherein the first distribution of apertures is associated with a first density, wherein the second distribution of apertures is associated with a second density, wherein the first density is greater than the second density, wherein the first distribution of apertures with the first density provides first cushioning characteristics for the sole member, wherein the second distribution of apertures with the second density provides second cushioning characteristics for the sole member, and wherein the second cushioning characteristics differ from the first cushioning characteristics due to differences between the second density and the first density.

2. The sole structure of claim 1, wherein the first distribution of apertures is located closer to a longitudinal midline of the sole member than is the second distribution of apertures.

3. The sole structure of claim 1, wherein the set of pinpoint apertures are arranged along a forefoot region, a midfoot region, and a heel region of the sole member.

4. The sole structure of claim 1, wherein the sole member includes a midline extending from a forefoot region of the sole member to a heel region of the sole member, and wherein a majority of the apertures disposed near the midline are associated with a greater density than apertures disposed away from the midline.

5. The sole structure of claim 1, wherein the set of pinpoint apertures are arranged to extend across substantially an entire lateral width of the sole member.

6. The sole structure of claim 1, wherein pinpoint apertures comprise between 5% and 20% of the lower surface of the sole member.

7. The sole structure of claim 1, wherein pinpoint apertures comprise between 10% and 30% of the lower surface of the sole member.

8. The sole structure of claim 1, wherein pinpoint apertures comprise between 15% and 50% of the lower surface of the sole member.

9. The sole structure of claim 1, wherein pinpoint apertures comprise over 50% of the lower surface of the sole member.

10. The sole structure of claim 1, wherein two or more of the pinpoint apertures of the first distribution are disposed close enough to one another so as to form a continuous opening.

11. The sole structure of claim 1, wherein the first distribution of apertures with the first density and the second distribution of apertures with the second density are selected and arranged to provide cushioning characteristics customized for a specific individual user.

12. A sole structure for an article of footwear, the sole structure comprising:
- a sole member having an outer surface that includes an upper surface and a lower surface;
- the sole member having a set of pinpoint apertures, wherein a majority of apertures of the set of pinpoint apertures have a diameter less than 1 mm;
- wherein the set of pinpoint apertures are disposed along the outer surface of the sole member to form at least a first distribution of apertures and a second distribution of apertures; and
- wherein the first distribution of apertures is associated with a first density, wherein the second distribution of apertures is associated with a second density, wherein the first density is greater than the second density, wherein the first distribution of apertures with the first density provides first cushioning characteristics for the sole member, wherein the second distribution of apertures with the second density provides second cushioning characteristics for the sole member, and wherein the second cushioning characteristics differ from the first cushioning characteristics due to differences between the second density and the first density.

13. The sole structure of claim 12, wherein the first distribution of apertures is located closer to a longitudinal midline of the sole member than is the second distribution of apertures.

14. The sole structure of claim 12, wherein pinpoint apertures comprise between 5% and 20% of the lower surface of the sole member.

15. The sole structure of claim 12, wherein pinpoint apertures comprise between 10% and 30% of the lower surface of the sole member.

16. The sole structure of claim 12, wherein pinpoint apertures comprise between 15% and 50% of the lower surface of the sole member.

17. The sole structure of claim 12, wherein pinpoint apertures comprise over 50% of the lower surface of the sole member.

18. The sole structure of claim 12, wherein two or more of the pinpoint apertures of the first distribution are disposed close enough to one another so as to form a continuous opening.

19. The sole structure of claim 12, wherein the first distribution of apertures with the first density and the second distribution of apertures with the second density are selected and arranged to provide cushioning characteristics customized for a specific individual user.

20. The sole structure of claim 12, wherein all apertures of the set of pinpoint apertures have a diameter less than 1 mm.

* * * * *